(12) United States Patent
Yan et al.

(10) Patent No.: US 11,031,557 B2
(45) Date of Patent: Jun. 8, 2021

(54) CONJUGATED POLYMERS BASED ON TERTHIOPHENE AND THEIR APPLICATIONS

(71) Applicant: RAYNERGY TEK INC., Hsinchu (TW)

(72) Inventors: He Yan, Hong Kong (CN); Huawei Hu, Xi'an (CN)

(73) Assignee: RAYNERGY TEK INC., Hsinchu (TW)

( * ) Notice: Subject to any disclaimer, the term of this patent is extended or adjusted under 35 U.S.C. 154(b) by 0 days.

(21) Appl. No.: 16/527,746

(22) Filed: Jul. 31, 2019

(65) Prior Publication Data

US 2020/0052217 A1    Feb. 13, 2020

Related U.S. Application Data

(63) Continuation of application No. 15/521,019, filed as application No. PCT/US2015/056895 on Oct. 22, 2015, now Pat. No. 10,446,756.

(Continued)

(51) Int. Cl.
| | |
|---|---|
| *H01L 51/00* | (2006.01) |
| *C08G 61/12* | (2006.01) |
| *C07D 409/14* | (2006.01) |
| *C07D 417/12* | (2006.01) |
| *C07D 417/14* | (2006.01) |

(Continued)

(52) U.S. Cl.
CPC ........ *H01L 51/0036* (2013.01); *C07D 409/14* (2013.01); *C07D 417/12* (2013.01); *C07D 417/14* (2013.01); *C08G 61/123* (2013.01); *C08G 61/124* (2013.01); *C08G 61/126* (2013.01); *C08G 2261/124* (2013.01); *C08G 2261/146* (2013.01); *C08G 2261/1412* (2013.01); *C08G 2261/18* (2013.01); *C08G 2261/3223* (2013.01); *C08G 2261/3229* (2013.01); *C08G 2261/3241* (2013.01); *C08G 2261/3246* (2013.01); *C08G 2261/334* (2013.01); *C08G 2261/344* (2013.01); *C08G 2261/364* (2013.01); *C08G 2261/414* (2013.01); *C08G 2261/514* (2013.01); *C08G 2261/91* (2013.01); *C08G 2261/94* (2013.01); *C08G 2261/95* (2013.01); *C08K 3/045* (2017.05); *H01L 51/0558* (2013.01); *H01L 51/42* (2013.01); *H01L 51/5296* (2013.01)

(58) Field of Classification Search
CPC ........................... C08G 61/126; C07D 409/14
See application file for complete search history.

(56) References Cited

U.S. PATENT DOCUMENTS

| | | |
|---|---|---|
| 8,298,686 B2 | 10/2012 | Uetani |
| 8,765,968 B2 | 7/2014 | Chen et al. |

(Continued)

FOREIGN PATENT DOCUMENTS

WO    WO2015020572 A1    2/2015

OTHER PUBLICATIONS

Fu et al. (Chemistry of Materials, 2012, 24, 4123-4133) (Year: 2012).

(Continued)

*Primary Examiner* — Liam J Heincer
(74) *Attorney, Agent, or Firm* — WPAT, PC

(57) ABSTRACT

Disclosed are conjugated polymers based on terthiophene. Such polymers exhibit good solubility and great solution processibility, and that enable highly efficient OPVs.

4 Claims, 12 Drawing Sheets

Related U.S. Application Data

(60) Provisional application No. 62/122,480, filed on Oct. 22, 2014.

(51) Int. Cl.
  *C08K 3/04* (2006.01)
  *H01L 51/05* (2006.01)
  *H01L 51/42* (2006.01)
  *H01L 51/52* (2006.01)

(56) References Cited

U.S. PATENT DOCUMENTS

| | | |
|---|---|---|
| 2003/0186079 A1 | 10/2003 | Towns et al. |
| 2007/0205714 A1 | 9/2007 | Busing et al. |
| 2011/0127512 A1 | 6/2011 | Goto et al. |
| 2011/0156018 A1 | 6/2011 | Moriwaki et al. |
| 2012/0061630 A1 | 3/2012 | Beaujuge et al. |
| 2013/0043434 A1 | 2/2013 | Tierney et al. |
| 2013/0090446 A1 | 4/2013 | Zhou et al. |
| 2013/0334520 A1 | 12/2013 | Amb et al. |
| 2014/0053905 A1 | 2/2014 | Byrne et al. |
| 2014/0175339 A1 | 6/2014 | Phillips et al. |
| 2015/0028265 A1 | 1/2015 | Yang et al. |
| 2015/0105520 A1 | 4/2015 | Bao et al. |
| 2015/0114467 A1 | 4/2015 | Su et al. |
| 2015/0132886 A1 | 5/2015 | Hayoz |
| 2015/0218304 A1 | 8/2015 | Wigglesworth et al. |
| 2015/0349257 A1 | 12/2015 | Li et al. |
| 2015/0357590 A1 | 12/2015 | Marks et al. |
| 2016/0141499 A1 | 5/2016 | Yan |
| 2016/0155947 A1 | 6/2016 | Kim et al. |
| 2016/0322575 A1 | 11/2016 | Yan |
| 2017/0301862 A1 | 10/2017 | Yan et al. |

OTHER PUBLICATIONS

Liang et al. (Marcomolecules, 2009, 42, 6107-6144) (Year:2009).

Zhou et al. (Angew Chem Int Ed. 2011, 50, 2995-2995) (Year: 2011).

CONJUGATED POLYMERS BASED ON TERTHIOPHENE AND THEIR APPLICATIONS

CROSS REFERENCE TO RELATED APPLICATIONS

This application is a Continuing Application of U.S. patent application Ser. No. 15/521,019, filed on Apr. 21, 2017.

BACKGROUND OF THE INVENTION

1. Field of the Invention

The present invention relates to novel polymer, methods for their preparation and intermediates used therein, the use of formulations as semiconductor in organic electronic (OE) devices, especially in organic photovoltaic (OPV) and organic field-effect transistor (OFET) devices, and to OE and OPV devices made from these formulations.

2. Description of the Prior Art

In recent years there has been growing interest in the use of organic semiconductors, including conjugated polymers, for various electronic applications.

One particular area of importance is the field of organic photovoltaics (OPV). Organic semiconductors (OSCs) have found use in OPV as they allow devices to be manufactured by solution-processing techniques such as spin casting and printing. Solution processing can be carried out cheaper and on a larger scale compared to the evaporative techniques used to make inorganic thin film devices. State-of-the-art OPV cells consist of a blend film of a conjugated polymer and a fullerene derivative, which function as electron donor and electron acceptor, respectively. In order to achieve highly efficient OPVs, it is important to optimize both the polymer (donor) and fullerene (acceptor) components and to find a material combination yielding an optimal BHJ morphology that supports efficient exciton harvesting and charge transport properties. Recent improvements in the efficiencies of single junction OPVs (efficiency ~8-9%) have largely been due to the development of low-band-gap polymers, which are defined as polymers with an absorption onset at least 750 nm or more and with a band-gap of 1.65 eV or less. (For example, a low-performance OPV polymer, P3HT, (bandgap~1.9 eV) is not considered the state-of-the-art polymers for OPVs.)

The low-band-gap polymer materials and the polymer/fullerene formulations that have been suggested in prior art for use in OPVs do still suffer from certain drawbacks. High-efficiency (>8%) OPVs can be achieved using many different low-band-gap polymers, which, however, are all constraint to use with a specific fullerene, $PC_{71}BM$, which is extremely expensive ($325/100 mg) and commercially unacceptable and which contains three isomers that are practically impossible to separate. Prior art indicated that the morphology and thus performance of the reported high-efficiency low-band-gap polymers are sensitive to the choice of fullerenes. Replacing $PC_{71}BM$ with another (cheaper) fullerene derivative, such as $PC_{61}BM$, or other non-PCBM fullerene, decreases the OPV efficiencies from 9.2% to 6-7%. To date, the progress in OPVs is "one-dimensional" from a materials perspective, with the emergence of many low band-gap donor polymers but with $PC_{71}BM$ being the dominant fullerene acceptor. The development of polymer/fullerene material systems whose morphology is insensitive to the choice of fullerene significantly increases the degrees of freedom in optimizing polymer/fullerene combinations and in exploring many different fullerene derivatives to achieve the best OPV performance.

SUMMARY OF THE INVENTION

In order to overcome the drawbacks of prior arts, the present invention provides various embodiments described below.

In certain embodiment, a conjugated polymer containing 5 or more repeating units of Formula (I) is provided:

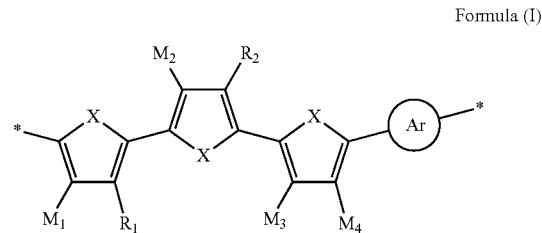

Formula (I)

wherein:
Ar is an aromatic unit that is not thiophene;
X is S or Se;
$M_1$, $M_2$, $M_3$, $M_4$ are independently selected from H or F; and
$R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups.

In certain embodiment, a conjugated polymer containing 5 or more repeating units of Formula (II) is provided:

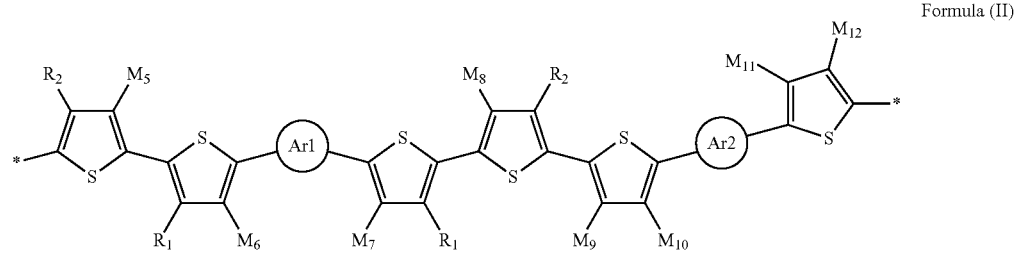

Formula (II)

wherein Ar1 and Ar2 are aromatic units that are not thiophene;

$M_5$, $M_6$, $M_7$, $M_8$, $M_9$, $M_{10}$, $M_{11}$, $M_{12}$ are independently selected from H or F; and $R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups.

In certain embodiment, a monomer for forming the above-mentioned conjugated polymer, with Formula (III) is provided:

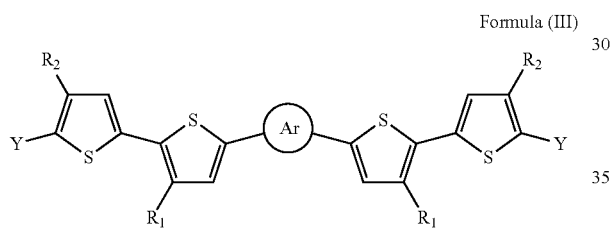

Formula (III)

wherein Ar is an aromatic unit that is not thiophene;

Y is Br or I;

$R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups; and Ar is selected from:

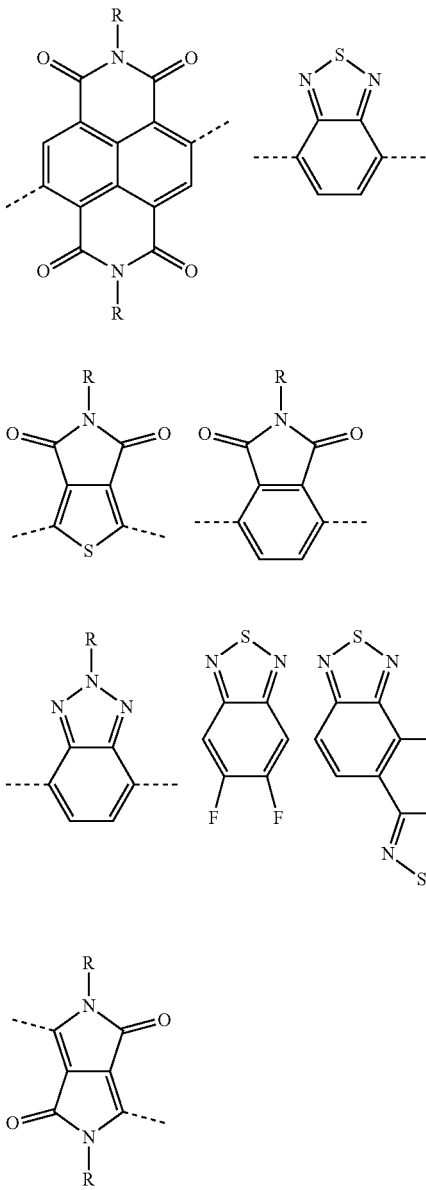

In certain embodiment, a conjugated polymer containing 5 or more repeating units of Formula (IV) is provided:

Formula (IV)

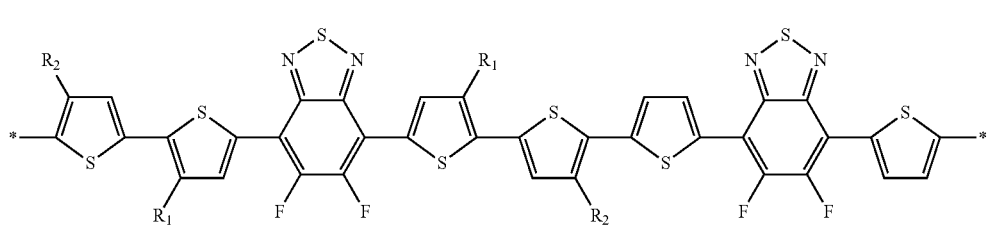

wherein $R_1$ and $R_2$ are independently selected from branched alkyl groups with 12-20 carbon atoms.

The above description is only an outline of the technical schemes of the present invention. Preferred embodiments of the present invention are provided below in conjunction with the attached drawings to enable one with ordinary skill in the art to better understand said and other objectives, features and advantages of the present invention and to make the present invention accordingly.

BRIEF DESCRIPTION OF THE DRAWINGS

The present invention can be more fully understood by reading the following detailed description of the preferred embodiments, with reference made to the accompanying drawings, wherein:

FIG. 1A shows chemical structures of the repeating units for bithiophene (T2), terthiophene (T3) and quaterthiophene (T4) based polymers. FIGS. 1B-1G show illustration of possible arrangements of alkyl chains on the oligothiophene units.

DETAILED DESCRIPTION OF THE PREFERRED EMBODIMENTS

Figure 1:
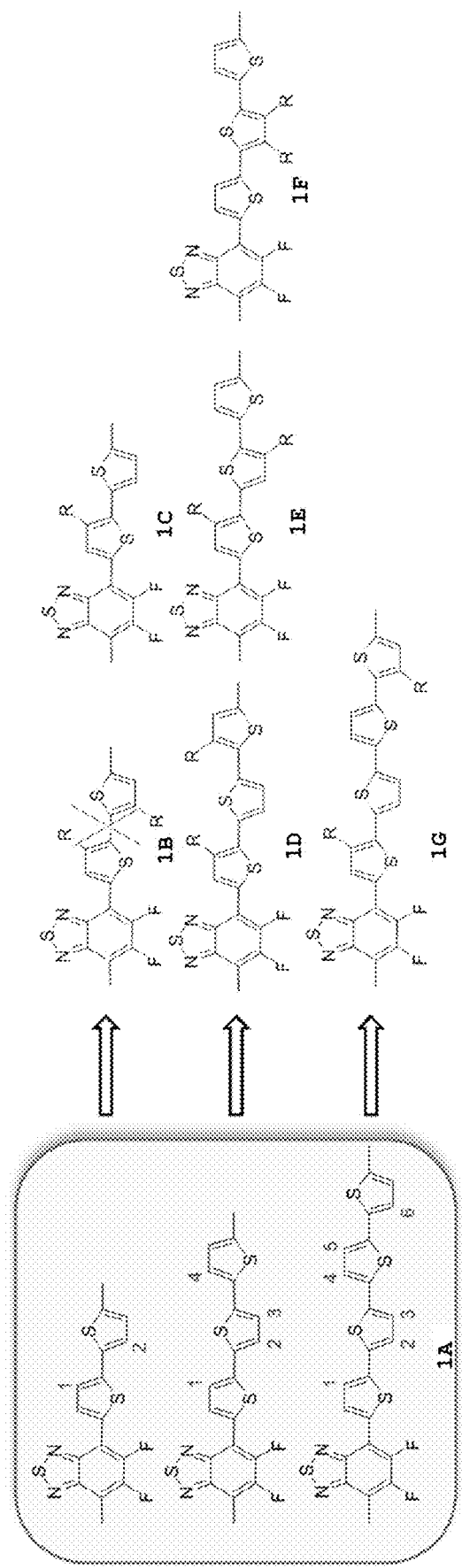
FIG. 1 shows chemical structures of the repeating units for bithiophene (T2), terthiophene (T3) and quaterthiophene (T4) based polymers and possible arrangements of alkyl chains on the oligothiophene units of the repeating units.

The present invention provides novel conjugated polymers, methods for their preparation and intermediates used therein, mixtures and formulations containing them, the use of the compounds, mixtures and formulations as semiconductor in organic electronic (OE) devices, especially in optical, electronic, or optoelectronic device comprising the conjugated polymer. The device is selected from an organic field-effect transistor(OFET), an organic light-emitting transistor, and an organic photovoltaic device(OPV). Additionally, the OE and OPV devices comprising these compounds, mixtures or formulations.

In the application, where an element or component is said to be included in and/or selected from a list of recited elements or components, it should be understood that the element or component can be one or more of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "contain", "contains", "containing", "include," "includes," "including," "have," "has," or "having" should be generally understood as open-ended and non-limiting unless specifically stated otherwise.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about 10$^{-5}$ cm/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about 10$^{-5}$ cm/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, (Pm or Vmp*Jmp), to the theoretical (not actually obtainable) power, (Jsc*Voc). Accordingly, FF can be determined using the equation:

$$FF=(Vmp*Jmp)/(Jsc*Voc)$$

where Jmp and Vmp represent the current density and voltage at the maximum power point (Pm), respectively, this point being obtained by varying the resistance in the circuit until J*V is at its greatest value; and Jsc and Voc represent the short circuit current and the open circuit voltage, respectively. Fill factor is a key parameter in evaluating the performance of solar cells. Commercial solar cells typically have a fill factor of about 0.60% or greater.

As used herein, the open-circuit voltage (Voc) is the difference in the electrical potentials between the anode and the cathode of a device when there is no external load connected.

As used herein, the power conversion efficiency (PCE) of a solar cell is the percentage of power converted from absorbed light to electrical energy. The PCE of a solar cell can be calculated by dividing the maximum power point (Pm) by the input light irradiance (E, in W/m2) under standard test conditions (STC) and the surface area of the solar cell (Ac in m2). STC typically refers to a temperature of 25° C. and an irradiance of 1000 W/m2 with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "semicrystalline polymer" refers to a polymer that has an inherent tendency to crystallize at least partially either when cooled from a melted state or deposited from solution, when subjected to kinetically favorable conditions such as slow cooling, or low solvent evaporation rate and so forth. The crystallization or lack thereof can be readily identified by using several analytical methods, for example, differential scanning calorimetry (DSC) and/or X-ray diffraction (XRD).

As used herein, "annealing" refers to a post-deposition heat treatment to the semicrystalline polymer film in ambient or under reduced/increased pressure for a time duration of more than 100 seconds, and "annealing temperature" refers to the maximum temperature that the polymer film is exposed to for at least 60 seconds during this process of annealing. Without wishing to be bound by any particular theory, it is believed that annealing can result in an increase of crystallinity in the polymer film, where possible, thereby increasing field effect mobility. The increase in crystallinity can be monitored by several methods, for example, by comparing the differential scanning calorimetry (DSC) or X-ray diffraction (XRD) measurements of the as-deposited and the annealed films.

Throughout the specification, structures may or may not be presented with chemical names. Where any question arises as to nomenclature, the structure prevails.

In a first embodiment of the present invention, a conjugated polymer containing 5 or more repeating units of Formula (I) is provided:

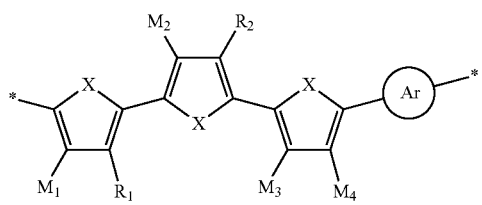

Formula (I)

wherein:
Ar is an aromatic unit that is not thiophene;
X is S or Se;
$M_1$, $M_2$, $M_3$, $M_4$ are independently selected from H or F; and
$R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups.

In this embodiment, $R_1$ and $R_2$ are independently selected from straight-chain or branched alkyl groups with 2-40 C atoms, and at least one of $R_1$ and $R_2$ is a branched alkyl group with 6-40 C atoms. More preferably, $R_1$ and $R_2$ are independently selected from branched alkyl groups with 6-40 C atoms.

More preferably, $M_1$, $M_2$, $M_3$, $M_4$ are H atom.

In this embodiment, Ar is selected from:

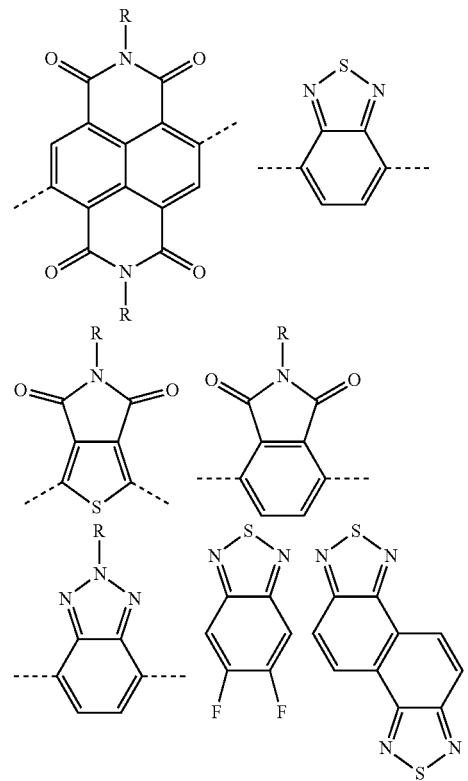

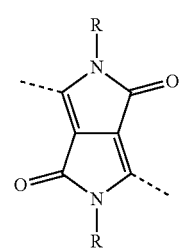

In certain embodiment, a composition comprising the above-mentioned conjugated polymer is disclosed. The composition is dissolved or dispersed in a liquid medium without using any processing additives, such as 1, 8-diiodooctane.

In a second embodiment of the present invention, a conjugated polymer containing 5 or more repeating units of Formula (II) is provided:

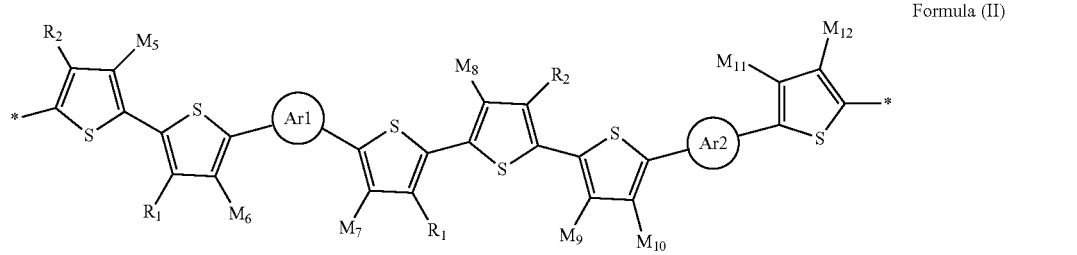

Formula (II)

wherein Ar1 and Ar2 are aromatic units that are not thiophene;

$M_5$, $M_6$, $M_7$, $M_8$, $M_9$, $M_{10}$, $M_{11}$, $M_{12}$ are independently selected from H or F; and $R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups.

In this embodiment, $R_1$ and $R_2$ are independently selected from straight-chain or branched alkyl groups with 2-40 C atoms, and at least one of $R_1$ and $R_2$ is a branched alkyl group with 6-40 C atoms. More preferably, $R_1$ and $R_2$ are independently selected from branched alkyl groups with 6-40 C atoms.

More preferably, $M_5$, $M_6$, $M_7$, $M_8$, $M_9$, $M_{10}$, $M_{11}$, $M_{12}$ are H atom.

In this embodiment, Ar1 and Ar2 are independently selected from:

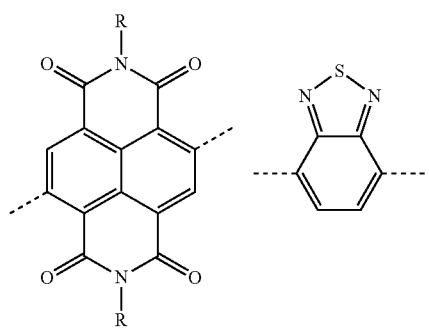

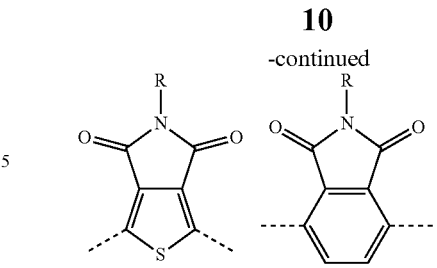

-continued

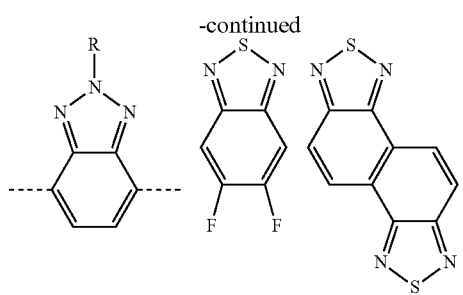

-continued

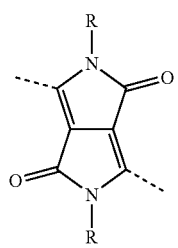

In certain embodiment, a composition comprising the above-mentioned conjugated polymer is disclosed. The composition is dissolved or dispersed in a liquid medium without using any processing additives, such as 1, 8-diiodooctane.

In certain embodiment, an organic photovoltaic device comprising a n-type semiconductor material adjacent to the above-mentioned conjugated polymer is disclosed. The n-type semiconductor material is fullerene derivative except for $PC_{71}BM$, or more preferably $PC_{61}BM$ or non-PCBM fullerene, and the power conversion efficiency is at least 9%.

In a third embodiment of the present invention, a monomer for forming the above-mentioned conjugated polymer, with Formula (III) is provided:

Formula (III)

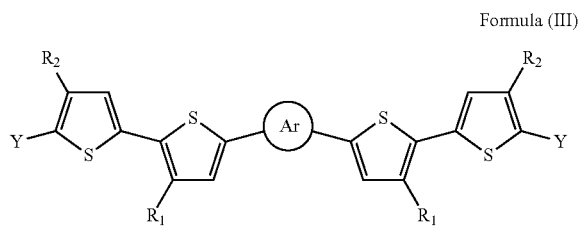

wherein Ar is an aromatic unit that is not thiophene;
Y is Br or I;
$R_1$ and $R_2$ are independently selected from straight-chain, branched or cyclic alkyl groups with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups; and
Ar is selected from:

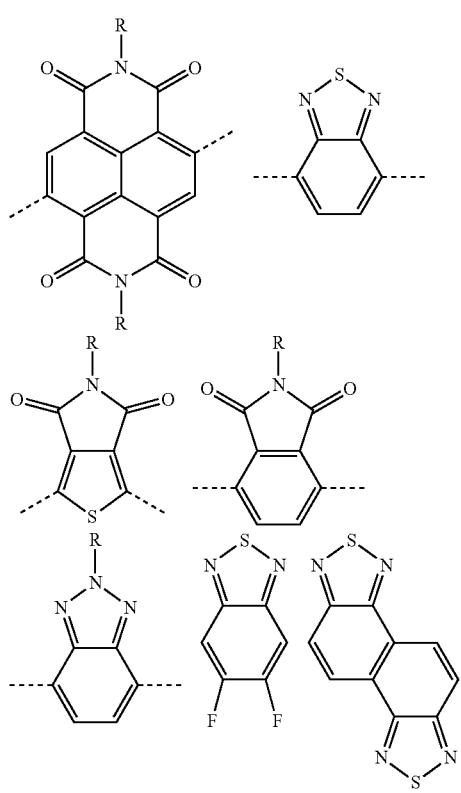

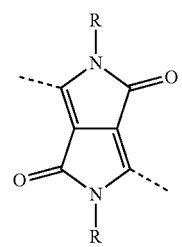

In this embodiment, more preferably, $R_1$ and R2 are independently selected from branched alkyl groups with 10-40 C atoms.

In a fourth embodiment of the present invention, a conjugated polymer containing 5 or more repeating units of Formula (IV) is provided:

Formula (IV)

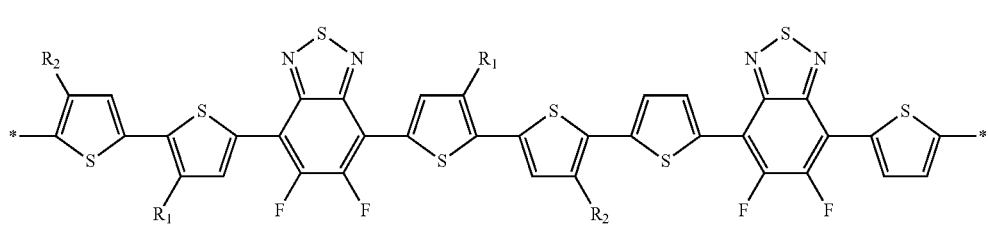

wherein $R_1$ and $R_2$ are independently selected from branched alkyl groups with 10-30 carbon atoms, or more preferably $R_1$ is C6C10 and $R_2$ is C6C9.

In certain embodiment, a composition comprising the above-mentioned conjugated polymer is disclosed. The composition is dissolved or dispersed in a liquid medium without using any processing additives, such as 1, 8-diiodooctane.

In certain embodiment, an organic photovoltaic device comprising a n-type semiconductor material adjacent to the above-mentioned conjugated polymer is disclosed. The n-type semiconductor material is fullerene derivative except for $PC_{71}BM$, or more preferably $PC_{61}BM$ or non-PCBM fullerene, and the power conversion efficiency is at least 9%.

In certain embodiments, a D-A polymer based on ffBT and terthiophene is disclosed. The D-A polymer is with an asymmetric arrangement of alkyl chains that enables the fabrication of highly efficient PSCs. The main design rationale for the new polymers is to increase the beneficial electronic effects of ffBT units by reducing the number of thiophene rings per repeating unit and thus increasing the effective density of ffBT units in the polymer backbone. This should enable further decreases in the HOMO and LUMO levels of the ffBT-oligothiophene polymers. Density functional theory (DFT) calculations were carried out on several polymer backbones (FIG. 1A) that have an increasing density of the ffBT units. The calculated HOMO and LUMO levels are −4.82 and −2.98, −4.88 and −3.02, −4.96 and −3.11 eV, for the T4, T3 and T2 polymers, respectively. The results of these DFT calculations indeed support the finding that deeper HOMO and LUMO levels can be obtained as the density of the ffBT unit increases.

Motivated by the positive results of the DFT calculation, several ffBT polymers based on quaterthiophene (T4), terthiophene (T3), and bithiophene (T2) units were synthesized. To obtain polymers that are soluble and easily processable for the fabrication of solar cells, it is important to attach branched alkyl chains on the beta positions of the thiophene rings. The use of second-position branched alkyl chains between the thiophene rings is critical, because they are the key structural feature that enables the highly temperature-dependent aggregation property of the polymers. Several possible arrangements of alkyl chins are illustrated in FIGS. 1B-1G. For the positioning of the alkyl chains, the first principle is to avoid putting two alkyl chains on the "head-to-head" positions of two adjacent thiophenes. For example, when positions 1 and 2 in the T2 polymer are attached with branched alkyl chains, the two thiophene units will be strongly twisted due to the steric hindrance effect caused by the two head-to-head alkyl chains (shown in FIG. 1B). Therefore, the T2 polymer has only one possible alkyl chain arrangement (FIG. 1C).

The common approach for the T4 polymer is to attach alkyl chains on the beta positions of the first and fourth thiophenes and allow the alkyl chains to point inside toward the second and third thiophene rings in a C2 symmetric manner (FIG. 1G). For the T3 polymers, there are three possible arrangements of alkyl chains on the terthiophene unit as shown in FIGS. 1D, 1E and 1F. Among these three possible arrangements, a reasonable and commonly used arrangement is to attach two alkyl chains on the first and third thiophene units in mirror symmetry with reference to the T3 unit (FIG. 1D), as reported in the literature. Another possibility is to attach the alkyl chains on the first and second thiophene units in a head-to-tail manner (FIG. 1E), which forms an asymmetric T3 unit; this appears to be an unusual manner of arranging alkyl chains on terthiophene. Surprisingly, we found that this unusual arrangement of alkyl chains (FIG. 1E) enabled a completely different and more favorable polymer:fullerene morphology and thus dramatically enhanced the performance of the PSCs compared with the reported approach of symmetric arrangement of alkyl chains on the T3 unit as shown in FIG. 1D. (Note that the 1f polymer was not successfully synthesized because the thiophene monomer substituted with two long-branched alkyl chains is extremely difficult to synthesize and purify.)

The synthesis of the new polymers involved in this study is illustrated in Scheme 1. The T4 polymer and the T3 polymer with alkyl chains on the first and third thiophenes (PffBT-T3(1,3)) can be synthesized via a commonly used synthetic route from the dibromide of 5,6-difluoro-4,7-bis(thiophen-2-yl)-2,1,3-benzothiadiazole (T-ffBT-T) and the distannyl reagent of thiophene or bithiophene. However, the synthesis of the T2 polymer or the other T3 polymers must be performed via a different route involving the distannyl reagent of T-ffBT-T. Note that each repeating unit of the T4 and T3(1,3) polymers contains only one ffBT unit, whereas the repeating units of the T2 and T3(1,2) polymers contain two ffBT units that are not chemically equivalent due to the different positions of the alkyl chains relative to those of the ffBT units.

Regarding the size of the alkyl chains, the common choices of second branched alkyl chains include 2HD (2-hexyldecyl, C6C10), 2OD (2-octyldodecyl, C8C12), and 2DT (2-decyltetradecyl, C10C14). As shown in our previous report, the choice of an optimal size for the alkyl chains is important to achieve the best performance. The general guideline of the choice of alkyl chain is to minimize the size of the branched alkyl chains, because unnecessarily long alkyl chains (such as 2DT) may cause many negative effects, including a reduced absorption coefficient, a lower domain purity, and lower efficiency for PSCs. At the same time, it is necessary to use an alkyl chain that is sufficiently large to provide sufficient solubility for the polymer. For the T3 polymers, the choices of alkyl chain are 2HD and 2HN (2-hexylnonyl, C6C9). For the T4 polymers, the choices of alkyl chain are 2HD and 2OD. However, the T2 polymers with 2HD, 2OD, and even 2DT alkyl chains exhibit extremely poor solubility. Therefore, an especially long alkyl chain of 2TH (2-tetradecylhexadecyl, C14C16) must be incorporated in the T2 polymer structure to obtain a polymer that is possible to process. In this study, we mainly examine the differences in the properties of PffBT-T4-2HD, PffBT-T3(1,2)-1, and PffBT-T2, which correspond to the T4, T3, and T2 polymers, respectively. Note that PffBT-T4-2HD and PffBT-T3(1,2)-1 were selected to compare the differences in the properties between the T4 and T3 polymers, because PffBT-T4-2HD and PffBT-T3(1,2)-1 have the same 2HD alkyl chains and allow a fair comparison between the solubility properties of the T4 and T3 polymers.

Figure 2A:
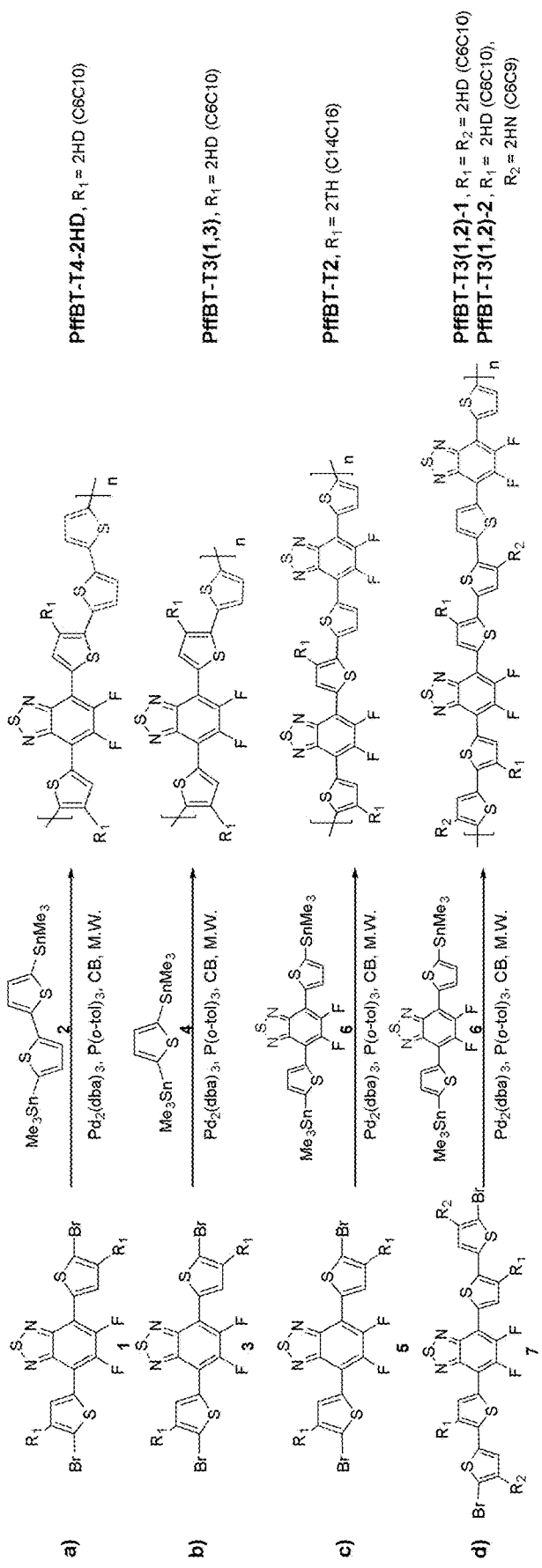
FIGS. 2A and 2B show normalized UV-Vis absorption spectra of polymer films.
Figure 2B:
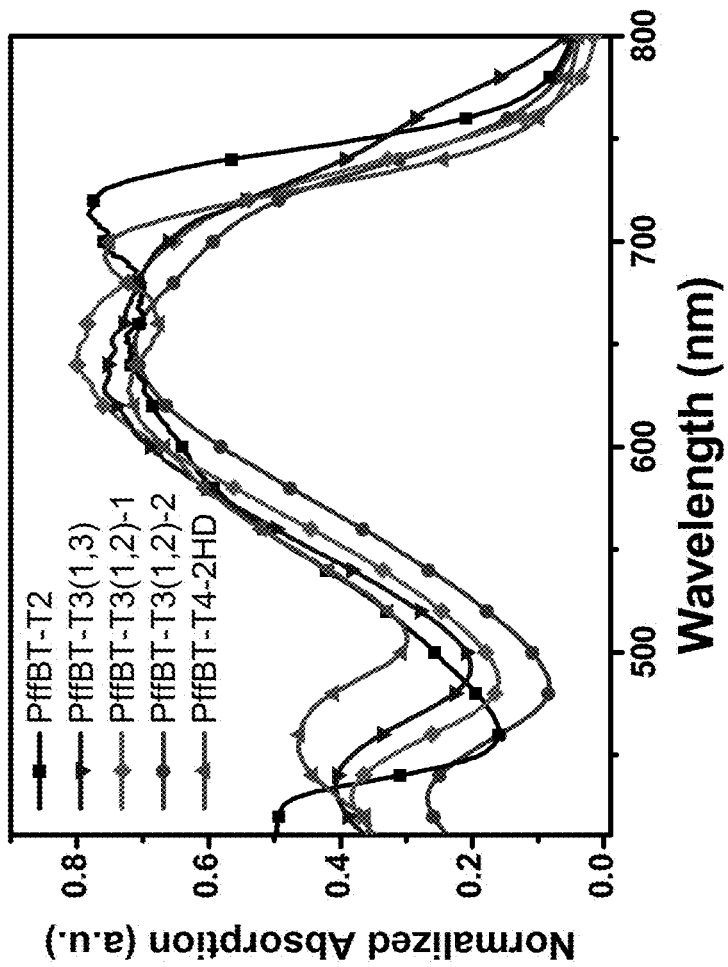
Figure 3B:
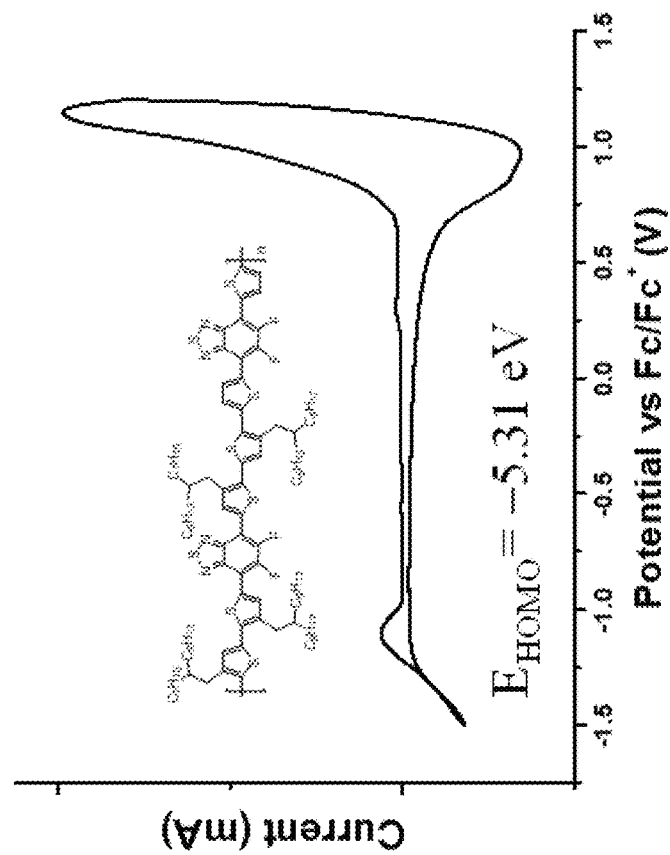
FIGS. 3A-3E show cyclic voltammograms of Polymer film in MeCN/0.1 M Bu$_4$NBF$_4$.
Figure 3A:
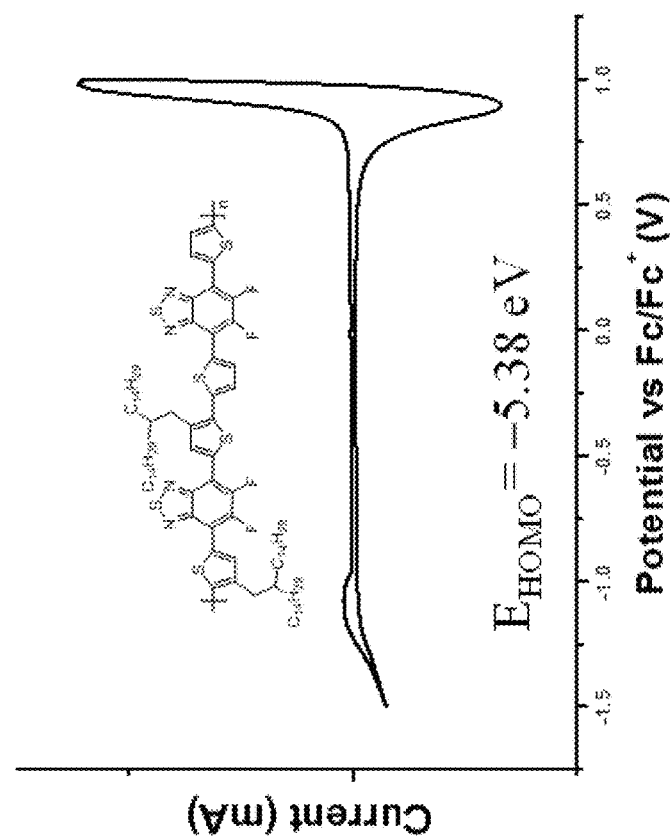
Figure 3C:
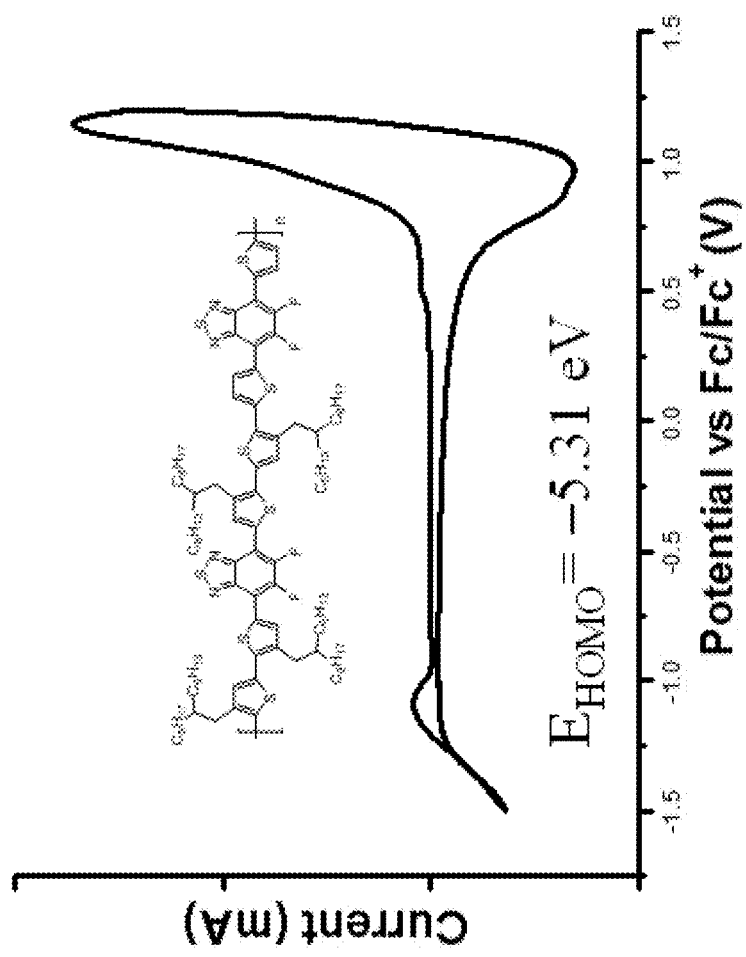
Figure 3E:
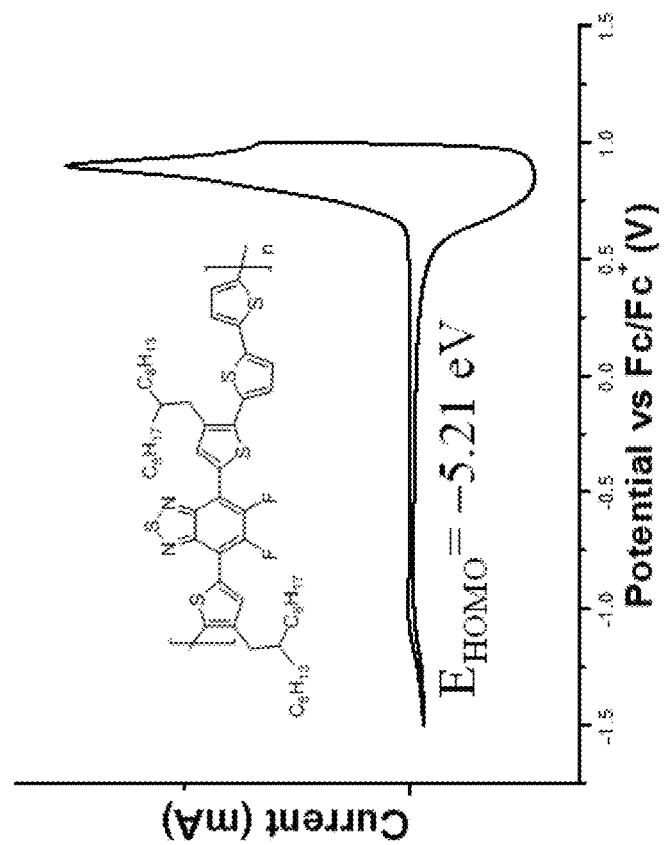
Figure 3D:
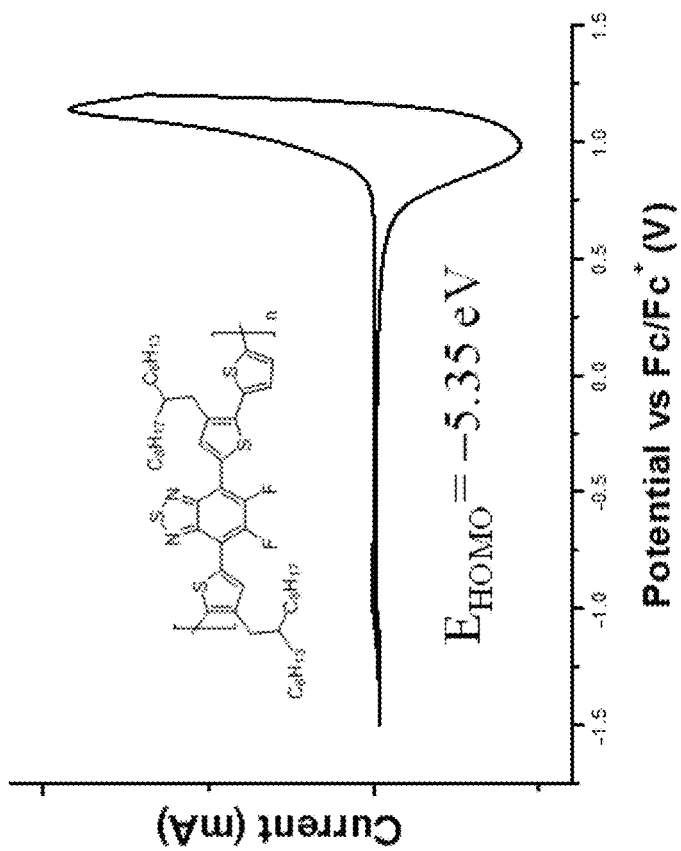
Figure 4B:
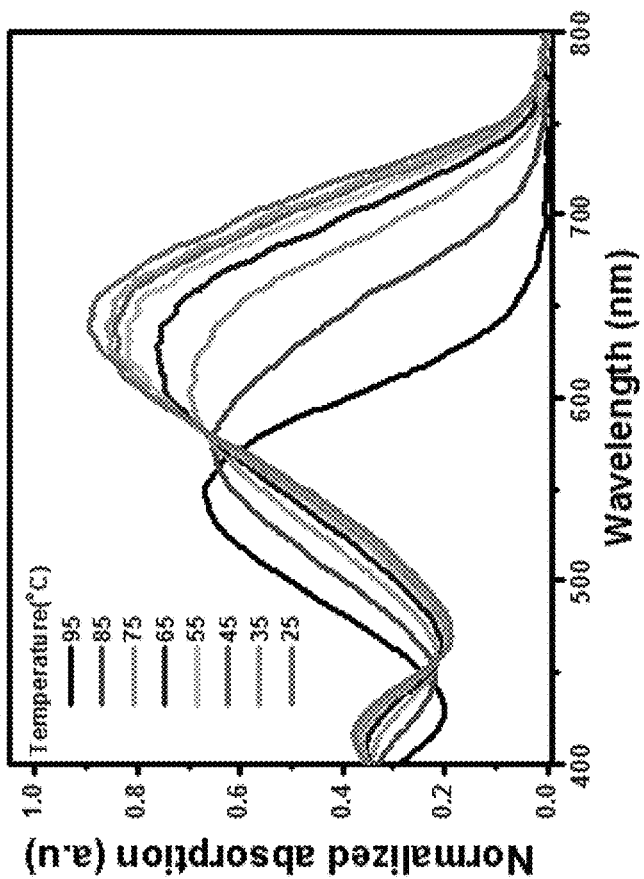
FIGS. 4A-4F show the evolutions of UV absorption spectra of polymers in CB (1×10$^{-5}$ M) during cooling process from 95 to 25° C. A) PffBT-T3(1,2)-2 with high molecular weight (Mn=66 kDa, Mw=109 kDa); B) PffBT-T3(1,2)-2 with low molecular weight (Mn=47 kDa, Mw=83 kDa); C) PffBT-T3(1,2)-1; D) PffBT-T3(1,3); E) PffBT-T4-2HD; F) PffBT-T2
Figure 4A:
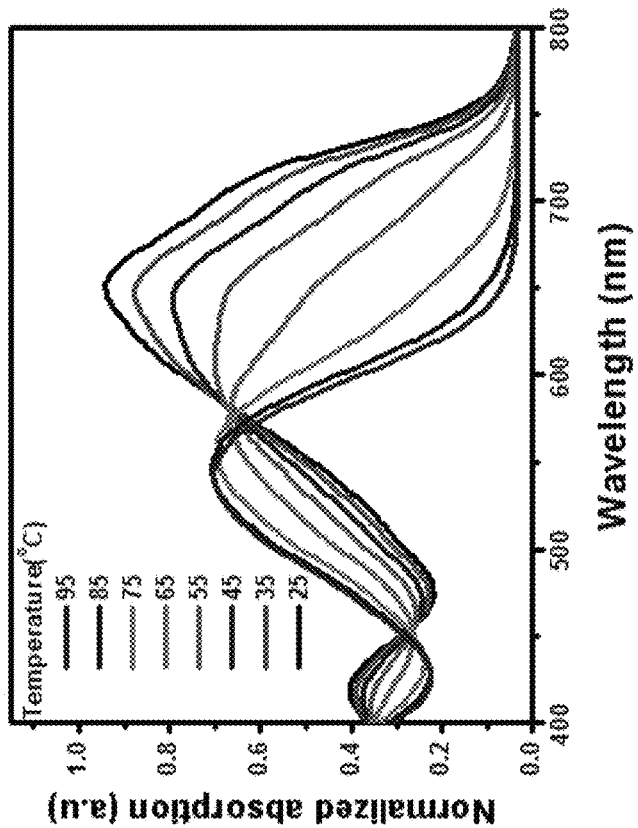
Figure 4D:
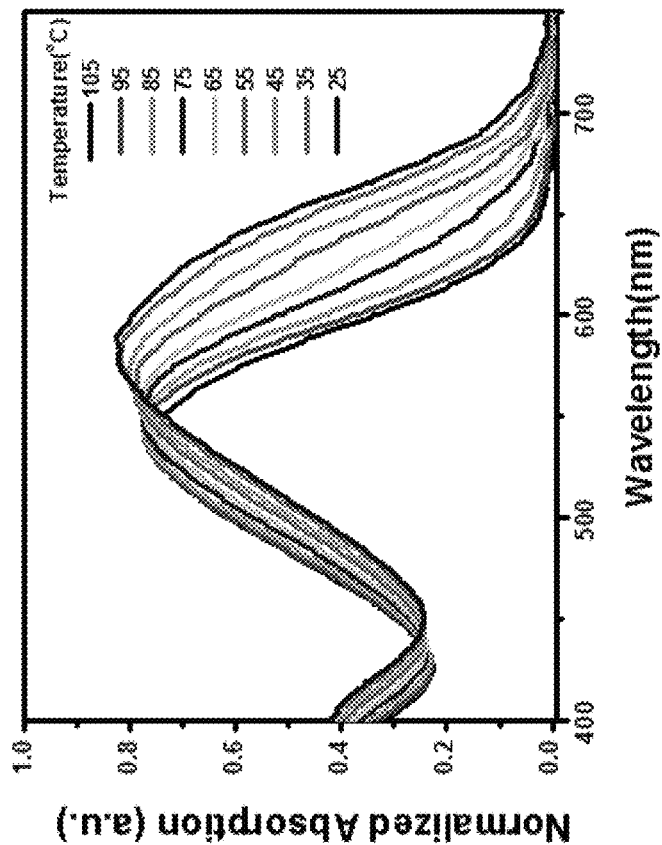
Figure 4C:
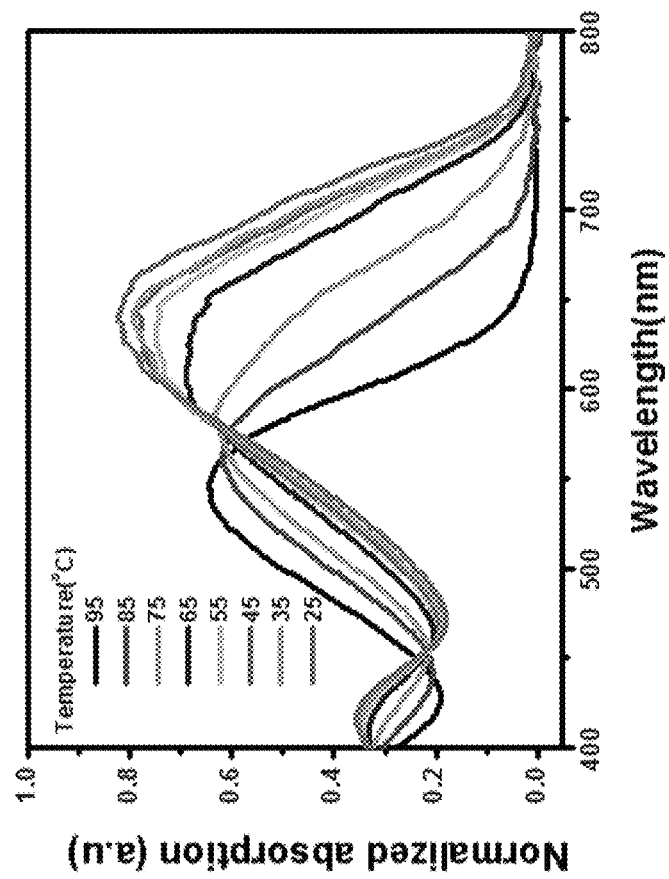
Figure 4F:
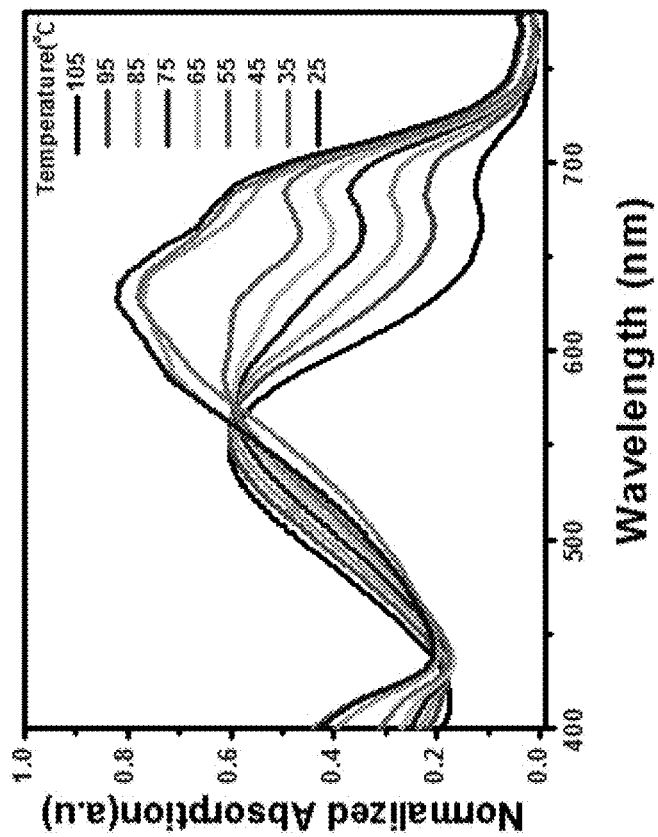
Figure 4E:
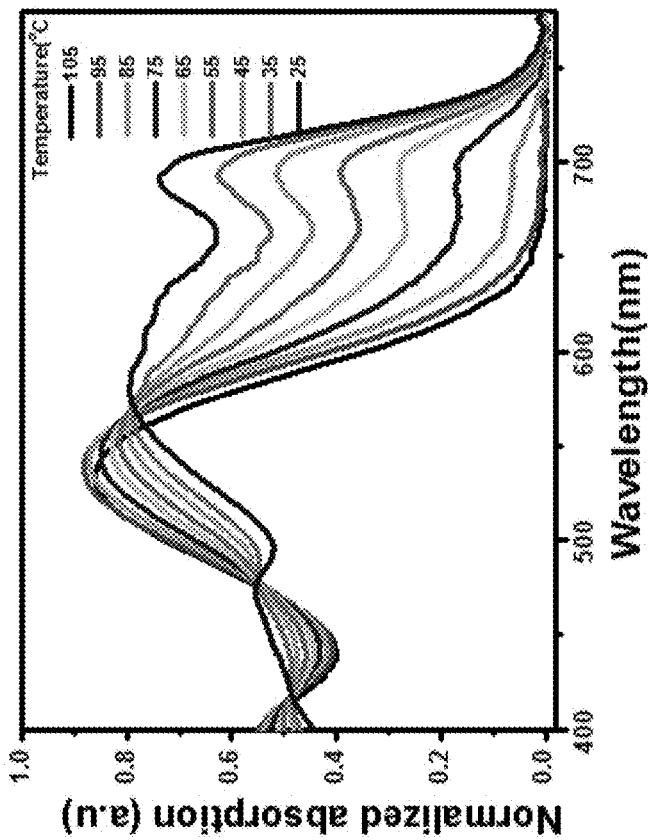

The optical bandgaps and energy levels of the investigated polymers (summarized in Table 1) were estimated on the basis of the film UV-Vis absorption spectra (FIG. 2B) and cyclic voltammetric measurements (FIG. 3A-3E). The T3 polymers indeed exhibit deeper HOMO and LUMO levels than the T4 polymers, which is consistent with the shift in HOMO levels predicted by the DFT calculations and with the change in the open circuit voltages ($V_{OC}$) of the corresponding PSCs (which will be shown later). The bandgaps of the polymers also slightly decrease as the number of thiophene units decreases (from T4 to T2). A deeper HOMO level and smaller bandgaps should help to achieve high $V_{OC}$ and larger short-circuit current ($J_{SC}$) for the PSCs. It is important to note that the LUMO level of the T2 polymer is −3.77 eV, which might be too deep to provide a sufficient LUMO offset with PCBM (LUMO, −4.0 eV), because it is commonly believed that a LUMO offset of 0.3 eV is needed to ensure highly efficient exciton dissociations.

TABLE 1

Optical and electrochemical properties of polymers.

| polymer | Mn (kDa) | Mw (kDa) | $E_{HOMO}$ (eV)[a] | $E_{g,opt}$ (eV)[b] | $E_{LUMO}$ (eV)[c] |
| --- | --- | --- | --- | --- | --- |
| PffBT-T4-2HD | 13.9 | 25.8 | −5.21 | 1.65 | −3.56 |
| PffBT-T3(1,3) | 37.7 | 56.0 | −5.35 | 1.60 | −3.75 |
| PffBT-T3(1,2)-1 | 72.2 | 129.0 | −5.31 | 1.63 | −3.68 |
| PffBT-T3(1,2)-2 | 66.1 | 109.6 | −5.31 | 1.63 | −3.68 |
| PffBT-T2 | 58.4 | 98.0 | −5.38 | 1.61 | −3.77 |

[a]Measured by cyclic voltammetry;
[b]Estimated based on film absorption onset;
[c]Calculated by using HOMO and $E_{g,opt}$.

Next, the solubility and crystallinity of the polymers are studied. The following discussions focus mainly on the comparison of the T3 and T4 polymers, both of which exhibit reasonably good PSC performance. The properties and performance of the T2 polymer will be explained separately in a later paragraph. (Regarding the T2 polymer, it exhibits an extremely poor solubility compared with the T3 and T4 polymers, because it has only one branched alkyl chain for each ffBT repeating unit and the T3 and T4 polymers have two branched alkyl chains for each repeating unit. The extremely poor solubility of the T2 polymer partially contributes to the poor PSC performance of the PffBT-T2-based devices.) Comparing the T3 and T4 polymers with the same 2HD alkyl chains (PffBT-T4-2HD and PffBT-T3(1,2)-1), the PffBT-T3(1,2)-1 polymer exhibits a significantly enhanced solubility. The molecular weight of PffBT-T4-2HD is only 14 kDa, yet it could not be dissolved in hot toluene but it is only soluble in hot chlorobenzene. In contrast, the PffBT-T3(1,2)-1 polymer with the same 2HD alkyl chains could be readily dissolved in toluene even though the polymer molecular weight is five times higher. The PffBT-T4-2HD polymer is found to be significantly more crystalline by grazing incidence wide angle x-ray scattering (GIWAXS). The (100) coherence length of PffBT-T4-2HD is about 17 nm, which is double that for the PffBT-T3(1,2)-1 polymer. Interestingly, the GIWAXS data shows that the percentage of face-on orientation in PffBT-T4-2HD:PC70BM blend film is almost 0%. The preferentially edge-on orientation of the PffBT-T4-2HD polymer backbone should reduce the charge transport ability of the polymer in the vertical direction, which partially explains the relatively low hole mobility of PffBT-T4-2HD despite its high crystallinity. In addition, the temperature-dependent aggregation properties of the T3 and T4 polymers are also compared. It can be clearly seen in FIGS. 4A-4F, the PffBT-T4-2HD polymer exhibits a strong absorption peak at 700 nm at room temperature, which indicates strong polymer aggregation in solution at room temperature. The PffBT-T3(1,2)-1 does not exhibit such an aggregation peak, indicating much weaker aggregation of the PffBT-T3(1,2)-1 polymer in solution.

Figure 5B:
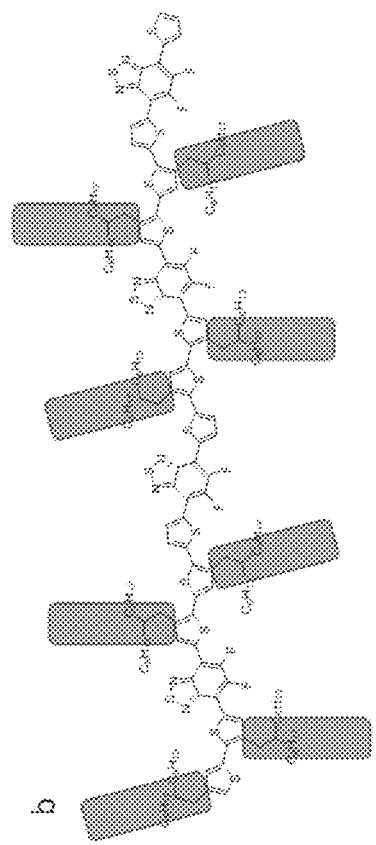
FIGS. 5A and 5B illustrates the orientations of alkyl chains on the PffBT-T4-2HD and PffBT-T3(1,2)-1 polymers.
Figure 5A:
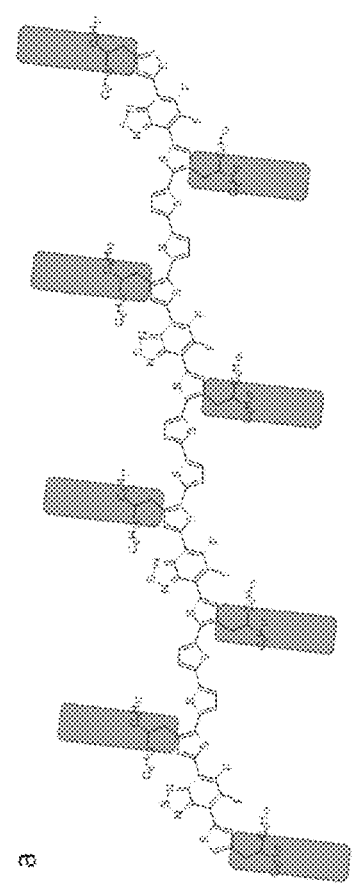

The greater solubility of the PffBT-T3(1,2)-1 compared with the PffBT-T4-2HD polymer is consistent with its lower crystallinity and weaker aggregation. It has been commonly observed in polymeric semiconductors that polymers with greater crystallinity often exhibit lower solubility because stronger π-π stacking between polymer chains makes it more difficult to dissolve the polymers. From the perspective of chemical structure, it is also reasonable for the PffBT-T4-2HD polymer to have greater crystallinity and stronger lamellar packing because the quaterthiophene comonomer (with two 2HD alkyl chains) has C2 symmetry, which allows the PffBT-T4-2HD polymer to form a regioregular polymer structure. As shown in FIG. 5A, the 2HD alkyl chains have a regular and parallel arrangement, which can help the interdigitation of the alkyl chains along the lamellar packing direction. The role of C2 symmetric monomers in the formation of regioregular polymer structures is well described in the literature. In contrast, the T3 unit is not C2 symmetric, and the 2HD alkyl chains on the PffBT-T3(1,2)-1 are not all parallel, which contributes to the lower extent of crystallinity of the PffBT-T3(1,2)-1 polymer. As a result, the extent of alkyl chain interdigitation is significantly stronger for the PffBT-T4-2HD polymer than for the PffBT-T3(1,2)-1 polymer, as evidenced by the small laminar stacking distance of the PffBT-T4-2HD polymer film (data summarized in Table 3).

TABLE 2

Photovoltaic properties of PSCs based on polymers/$PC_{71}BM$

| Polymer | $V_{OC}$ (V) | $J_{SC}$ (mA cm$^{-2}$) | FF (%) | PCE (%) |
|---|---|---|---|---|
| PffBT-T4-2HD | 0.73 ± 0.01 | 14.8 ± 0.2 | 64.4 ± 0.6 | 7.0 ± 0.2 |
| PffBT-T3(1,3) | 0.77 ± 0.01 | 10.6 ± 0.3 | 45.3 ± 0.9 | 3.7 ± 0.2 |
| PffBT-T3(1,2)-1 | 0.82 ± 0.01 | 18.5 ± 0.2 | 64.1 ± 0.7 | 9.7 ± 0.3 |
| PffBT-T3(1,2)-2 | 0.82 ± 0.01 | 18.7 ± 0.2 | 68.3 ± 0.5 | 10.5 ± 0.2 |
| PffBT-T2 | 0.88 ± 0.01 | 10.1 ± 0.3 | 48.6 ± 0.5 | 4.3 ± 0.2 |
| PffBT-T4-2OD | 0.77 ± 0.01 | 18.2 ± 0.2 | 73.2 ± 0.7 | 10.2 ± 0.3 |

The values for $V_{OC}$, $J_{SC}$ and FF are averages of about 15 devices.

Figures 6A, 6B:
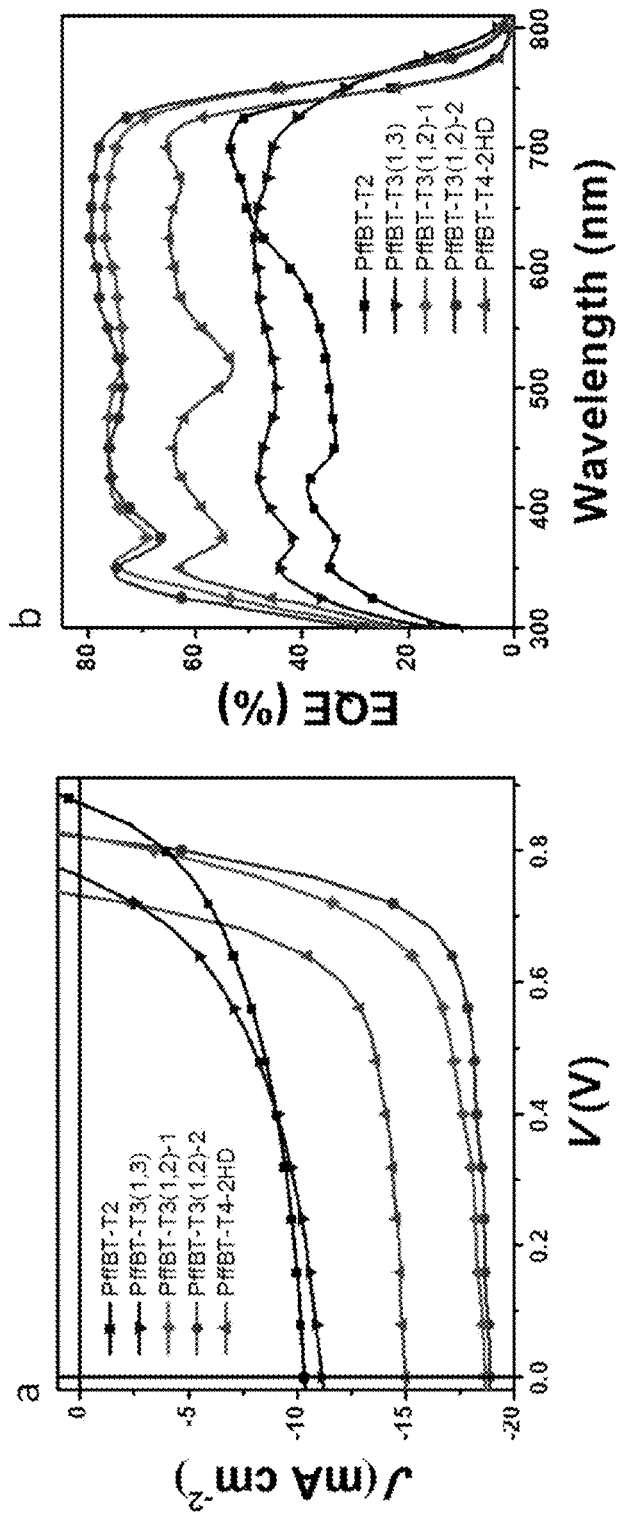
FIG. 6A shows current-voltage plots under illumination with AM 1.5G solar simulated light (100 mW/cm$^2$)
FIG. 6B shows EQE spectra of the BHJ solar cells with PC$_{71}$BM.

The performance of the PSC devices was investigated using an inverted device structure (ITO/ZnO/Polymer: $PC_{71}BM/V_2O_5/Al$). The characteristic current density-voltage curves of the optimized devices based on these five materials are presented in FIG. 6A. For the T4 polymer with 2HD alkyl chains (PffBT-T4-2HD), a PCE of 7.0% (7.2% max.) with a $V_{OC}$ of 0.73 V, a $J_{SC}$ of 14.8 mA cm$^{-2}$, and a fill factor (FF) of 64.4%, was obtained. Previous studies have shown that the optimal choice of alkyl chain for the T4 polymer is 2OD and that it is important to obtain reasonably high molecular weights to achieve high-efficiency devices. The use of 2HD alkyl chains on PffBT-T4-2HD caused less solubility and lower molecular weights (~14K) than the T4 polymer with 2OD alkyl chains, thus leading to lower PCEs. The performance of the T4 polymer with 2OD alkyl chains have been reported and listed in Table 2 (the average efficiency of PffBT-T4-2OD:$PC_{71}BM$ devices is 10.2%).

In comparison, the T3 polymer exhibits significantly enhanced solubility. As a result, even the T3 polymer with the 2HD alkyl chain exhibits excellent solubility for device processing. For PffBT-T3(1,2)-1, a $V_{OC}$ as high as 0.82 V was observed, combined with its high $J_{SC}$ of 18.5 mA cm$^{-2}$ and FF of 64.1%, a high PCE of 9.7% (10.0% max.) was obtained. As the solubility of PffBT-T3(1,2)-1 is still more than sufficient, the size of the alkyl chains on PffBT-T3(1,2)-1 could be further reduced to minimize potential negative effects of alkyl chains. For this reason, a T3 polymer with a combination of 2HD and 2-hexylnonyl (2HN) alkyl was synthesized (structure shown in Scheme 1). Devices based on PffBT-T3(1,2)-2 showed a PCE of 10.5% (10.7% max.) with $V_{OC}$=0.82 V, $J_{SC}$=18.7 mA cm$^{-2}$, and FF=68.3%. Both the $J_{SC}$ and FF are better for the cells based on PffBT-T3(1,2)-2 than for the cells based on PffBT-T3(1,2)-1. (The structure-performance relationship of the two PffBT-T3(1,2) polymers can be understood by their morphological data, which are shown in the next paragraph). The $V_{OC}$ of the T4-polymer-based cells is 0.77 V, and that of the cells based on T3 polymers is about 0.82 V; this difference can be attributed to the deeper HOMO level of the T3 polymers. In addition, the onset of the absorption and external quantum efficiency (EQE) spectra (FIG. 6B) of the T3 polymers is red-shifted by ~10 nm compared with that of the T4 polymers, which contributes to the enhanced $J_{SC}$ of the PffBT-T3(1,2)-2 cells. Importantly, the high performance of the PffBT-T3(1,2)-2-based cells was achieved without using the undesirable DIO additive in the active layer processing. These results clearly indicate the beneficial effects of reducing the number of thiophenes and increasing the effective density of the ffBT units.

Figure 7:
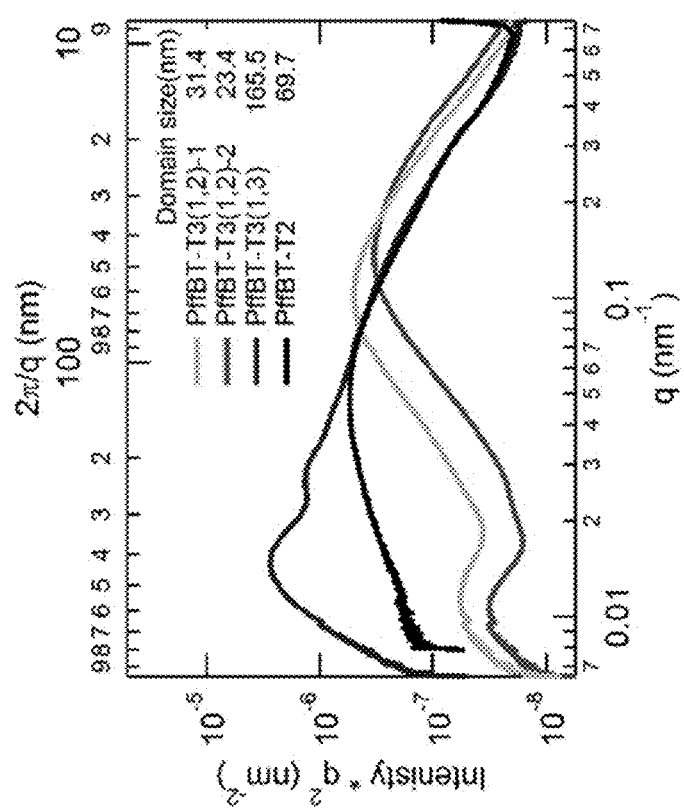
FIG. 7 shows R-SoXS data of Polymer:fullerene blend films.

Further studies on polymer:fullerene morphology by GIWAXS and resonant soft X-ray scattering (RSoXS) also reveal significant differences between the polymer:fullerene morphology for T3- and T4-based polymers. The change of the oligothiophene unit from T4 to T3 has both positive and negative effects on the polymer:fullerene morphology. The negative effect is that the two PffBT-T3(1,2) polymers are significantly less crystalline than the T4-based polymers, as explained in an earlier paragraph. The positive effect is that the median domain sizes (estimated by RSoXS, FIG. 7) of the polymer:fullerene blends based on the T3 polymers are reduced from 40 nm for PffBT-T4-2OD to about 31 nm for PffBT-T3(1,2)-1 and 23 nm for PffBT-T3(1,2)-2. The reduced domain size should be beneficial for the performance of PSCs because the 40 nm domain size of PffBT-T4-2OD is slightly larger than the generally accepted optimal domain size (20 to 30 nm) for PSCs.

On the other hand, the reduced extent of polymer crystallinity led to slightly lower fill factors (68.3%) for the PSCs based on T3 polymers than for their T4 counterparts (73.2%). Still, the FF of 68.3% for PffBT-T3(1,2)-2 is an impressive value, as the thickness of the active layer is relatively thick (~250 nm). It is well known that achieving high FFs for thick-film PSCs is quite challenging. The change in FF is consistent with the reduced space charge limited current (SCLC) hole mobility of the T3-based polymers in comparison with that of the T4-based polymers. As shown in Table S1, the SCLC hole mobilities of PffBT4T-2OD and PffBT3T(1,2)-2 are about $1.2 \times 10^{-2}$ and $2.4 \times 10^{-3}$ $cm^2$ $V^{-1}s^{-1}$, respectively. Nevertheless, the overall PSC performance of the devices based on PffBT-T3(1,2)-2 is improved because the benefits of an increased Voc, widened absorption ranges, and a reduced domain size outweighs the loss in FF due to the weaker polymer crystallinity. The results show that a change of the comonomer structure from T4 to T3 provides an important tool to optimize the energy levels and the morphology of the polymer:fullerene blends, which results in an overall beneficial effect that led to enhanced PSC efficiencies even without using the DIO additive. Previous study[48] has shown that the use of DIO is critical for PTB7:$PC_{71}$BM-based materials in order to achieve small domain sizes of ~20 nm that is optimal for PSC operation. In our study, however, the blend of PffBT-T3(1,2)-2:$PC_{71}$BM exhibits an optimal domain size without using the DIO additive in the solution.

Our comparison of the structures, morphology, and performance of the other two T3 polymers PffBT-T3(1,2)-1 and PffBT-T3(1,2)-2 also provide interesting results. While PffBT-T3(1,2)-1 has two 2HD alkyl chains, PffBT-T3(1,2)-2 has one 2HD alkyl chains and one slightly shorter 2HN alkyl chain on each terthiophene repeating unit. The design rationale of PffBT-T3(1,2)-2 is to slightly reduce the alkyl chains and the solubility of PffBT-T3(1,2)-1 and thus to increase the crystallinity and hole mobility of the polymer. Indeed, the GIWAXS data show that the (010) CL of PffBT-T3(1,2)-2 increases to 3.97 nm, whereas that of PffBT-T3(1,2)-1 is 3.19 nm. The (010) d-spacing of PffBT-T3(1,2)-2 is also slightly reduced from 3.67 to 3.65 Å. The lamellar stacking of PffBT-T3(1,2)-2 is also stronger than that of PffBT-T3 (1,2)-1; the (100) CL increases from 8.01 to 8.51 nm and the (100) d-spacing decreases from 19.81 to 19.27 nm. The SCLC hole mobility of PffBT-T3(1,2)-2 based cells is $2.4 \times 10^{-3}$ $cm^2$ $V^{-1}$ $s^{-1}$ which is double that of the cells based on PffBT-T3(1,2)-1 ($1.2 \times 10^{-3}$ $cm^2V^{-1}$ $s^{-1}$). Although the greater crystallinity of PffBT-T3(1,2)-2 than PffBT-T3(1,2)-1 is the expected result of the reduced alkyl chain size, it is surprising to observe that the domain size of polymer:fullerene blends is significantly smaller for PffBT-T3(1,2)-2 (23.5 nm) than for PffBT-T3(1,2)-1 (31 nm). The reduced domain size of PffBT-T3(1,2)-2 is possibly due to the fact that the polymer contains a mixture of 2HD and 2HN alkyl chains, which appears to have a positive effect on reducing the domain size of polymer:fullerene blends.

TABLE 3

Summary of GIWAXS data.

| Materials | (100) d spacing (Å) [±0.01] | (100) Crystal size (Å) [±3.0] | (010) d spacing (Å) [±0.01] | (010) Crystal size (Å) [±0.7] | Percentage of face-on area (%) [±2] |
| --- | --- | --- | --- | --- | --- |
| PffBT-T4-2HD:$PC_{71}$BM | 18.18 | 170.4 | 3.50 | 78.4 | 0 |
| PffBT-T3(1,3):$PC_{71}$BM | 21.61 | 159.1 | 3.47 | 48.4 | 68 |
| PffBT-T3(1,2)-1:$PC_{71}$BM | 19.81 | 80.1 | 3.67 | 31.9 | 100 |
| PffBT-T3(1,2)-2:$PC_{71}$BM | 19.27 | 85.1 | 3.65 | 39.7 | 100 |
| PffBT-T2:$PC_{71}$BM | 24.09 | 129.1 | 3.48 | 75.8 | 100 |

The values in brackets represent typical errors of the measurements.

It is important that the three T3 polymers can achieve significantly different PSC performance despite the relatively small differences in their chemical structures. The T3 polymer (PffBT-T3(1,3)), with a known and symmetric arrangement of alkyl chains exhibit the worst performance. In such an arrangement, the two 2HD alkyl chains are pointed toward each other in a head-to-head manner with only one thiophene spacer. This could have resulted in a significant steric hindrance effect and thus limit the molecular weight of the polymer. The molecular weight of PffBT-T3(1,3) is 37.7 kDa, which is significantly lower than that of the other two T3-based polymers. It is also found that the polymer:fullerene domain size (estimated by RSoXS) for PffBT-T3(1,3) is 165 nm, which is excessively large for optimal PSC operation. PffBT-T3(1,3) exhibits greater crystallinity than the other two T3 polymers, as shown by its large (010) and (100) coherence lengths (CL). However, the hole mobility of PffBT-T3(1,3) is the worst ($6.7 \times 10^{-4}$ $cm^2$ $V^{-1}$ $s^{-1}$), because it does not have a preferential face-on orientation like those of the other two T3 polymers. In contrast, both PffBT-T3(1,2)-1 and PffBT-T3(1,2)-2 films exhibit a (010) peak that is preferentially located in an out-of-plane direction. These negative morphological features can largely explain the poor PSC performance of cells based on PffBT-T3(1,3).

For the T2 based polymer, its PSC performance is significantly worse than that of the best T3 and T4 polymers. First, the solubility of the T2 based polymers is extremely poor, because there is only one alkyl chain for each ffBT unit. As a result, when 2HD or 2OD alkyl chains were used on the T2 polymer backbone, the solubility of the obtained polymers is too poor to be soluble in hot chlorobenzene. Even when a much longer 2DT alkyl chain is used on the T2 polymer backbone, the polymer obtained is only slightly soluble in boiling chlorobenzene. The molecular weight of the T2 polymer with 2DT alkyl chains is only 5 kDa, because the MW is limited by the poor solubility of the polymer. As a result, an excessive long alkyl chain (2TH) is used on the T2 polymer backbone to obtain a polymer that has reasonably high molecular weight and good solubility. In previous report,[5] excessively long alkyl chains have been shown to have many negative effects such as impure domains and poor lamellar stacking. As the 2DT alkyl chain was already proved to be excessively long and to have caused several negative effects in our report, the current 2TH alkyl chains have six additional carbons compared to 2DT and are likely to cause more serious negative effects. In addition, the LUMO level of the T2-based polymer is −3.77 eV, which may be too deep to offer a sufficient LUMO offset to ensure efficient exciton dissociation.

It is well known that polymer molecular weight is an important material parameter that could influence polymer aggregation and the morphology of the polymer:fullerene blend.[53-56] Therefore, it is important to study the effect of molecular weights on the performance of the PffBT-T3(1,2)-2 polymer. While the polymer batch with the best 10.7% efficiency has a Mn of 66.1 kDa, a lower molecular weight (Mn=47.8 kDa) polymer batch was intentionally synthesized for comparison (Table S2). Firstly, the lower molecular weight polymer batch exhibits a better solubility as it can be extracted using chloroform. In contrast, the higher molecular weight polymer is not soluble in hot chloroform and can only be extracted using hot toluene or chlorobenzene. The temperature dependent aggregation properties of these two polymer batches are then compared in FIGS. 4A-4F. Overall, the shape and the trend of red-shift for the UV-Vis absorption spectra of the two polymer batches are rather similar. The absorption spectra of the higher MW polymer are only slightly different with a small shoulder at about 730 nm (FIG. 4A-4F). PSC devices were fabricated based on the lower molecular weight PffBT-T3(1,2)-2 polymer and a respectably high efficiency of 10.2% was obtained. These results show that the PffBT-T3(1,2)-2 polymer can yield high-performance (>10%) PSCs when the polymer batches have lower polymer molecular weights and very different solubility properties. This is an important advantage for the scale-up of polymer batches as there is less stringent requirement to control the molecular and solubility properties of the polymer.

It is also noted that some polymers in Table 1 have significantly lower molecular weights than PffBT-T3(1,2)-2. Therefore, it is important to clarify whether the lower molecular weight is the reason that caused their inferior PSC performance. For the PffBT-T4-2HD polymer (Mn=13.9 kDa), our main conclusion was that it exhibits much poorer solubility than the PffBT-T3 polymers. If the low MW version of PffBT-T4-2HD already exhibits dramatically lower solubility than the PffBT-T3 polymer, the solubility of higher MW version should be even worse. To prove this point, we attempted to synthesize the PffBT-T4-2HD polymer with higher molecular weights. Due to the poor solubility of the PffBT-T4-2HD polymer, it tends to solidify in the polymerization reaction glassware once the molecular weight reaches a certain level. It is thus generally challenging to synthesize polymers with higher molecular weights. By further synthesis optimizations, a PffBT-T4-2HD polymer batch was obtained with a high Mn of 65.6 kDa. Not surprisingly, the solubility of this polymer batch is much poorer and its processing is extremely difficult compared to the low MW batch. For the processing of the polymer:fullerene solution, the lower molecular weight PffBT-T4-2HD polymer can be processed at 110° C., but the higher molecular weight polymer requires the solution and substrate be pre-heated at 130-140° C. (the substrate also needs to attached onto a preheated metal chuck and spun together on the spincoater; the preheated metal chuck serves as a "heat reservoir" to slow down the cooling of the substrate during the spincoating process) to obtain a workable active layer film. The poor solubility of the high MW PffBT-T4-2HD polymer led to lower PSC efficiencies of 6.4% (6.2% max). With these new data, now we can compare different polymers with similar molecular weights (PffBT-T3(1,2)-2, Mn=47-66 kDa, PCE=10.2-10.7%; PffBT-T3(1,3), Mn=37.3 kDa, PCE=3.9%; PffBT-T4-2HD, Mn=65.6 kDa, PCE=6.4%; PffBT-T2, Mn=58.4 kDa, PCE=4.5%), it is clear that the dramatically higher performance of the higher performance of PffBT-T3(1,2)-2 than the other polymers is not due to molecular weights, instead, it is due to the terthiophene unit and the asymmetrical alkyl chain arrangement.

In summary, a series of ffBT and oligothiophene-based D-A copolymers are synthesized and systematically studied. It is shown that the T3 polymer with an asymmetric arrangement of alkyl chains enables highly efficient thick-film PSCs with PCE up to 10.7%. In addition, this high efficiency of T3 polymer-based PSCs was achieved without using any processing additives, which greatly simplifies of the processing of PSCs and makes the polymer more suitable for industry applications. By reducing the number of thiophene units per repeating unit, the HOMO and LUMO levels of the polymers are reduced and the absorption onsets of the polymer films are also slightly red-shifted. These positive changes contribute to higher Voc and Jsc values for the T3 polymer than for the T4 polymers. By comparing the three T3 polymers that differs in the positions and size of their alkyl chains, it is surprisingly found that the T3 polymer with an unusual head-to-tail arrangement of alkyl chains on the first and second thiophenes exhibit a more favorable morphology and dramatically enhanced performance than the T3 polymer with mirror-symmetric alkyl chains on the first and third thiophenes. Our study also show that the change from a T4 to a T3 comonomer unit introduces significant differences in the energy levels, solubility, crystallinity, polymer:fullerene morphology, and PSC performances between the T3 and T4 polymers. The polymer design rationales (using a T3 unit with an asymmetric arrangement of alkyl chains) demonstrated in our work provide an effective approach to tune the energy levels and morphology of donor polymers that can be adopted to further increase the efficiency of PSCs.

The following examples are provided to illustrate further and to facilitate the understanding of the present teachings and are not in any way intended to limit the invention.

EXAMPLE 1

Synthesis of Monomers

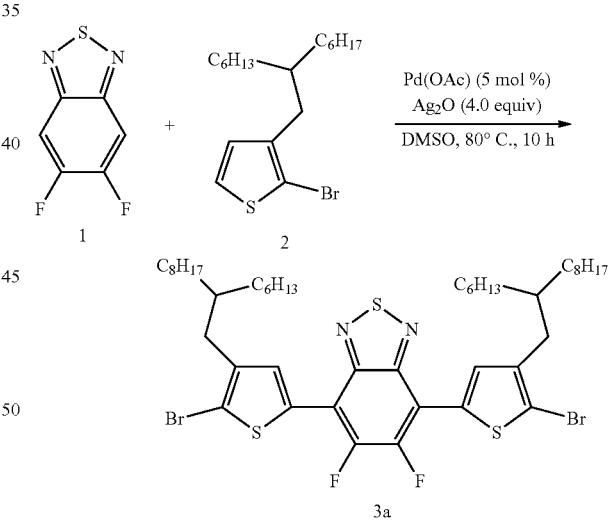

5,6-Difluoro-4,7-bis(4-(2-hexyldecyl)-2-thienyl)-2,1,3-benzothiadiazole (4)

To a solution of 1 (172 mg, 1.0 mmol), Pd(OAc)$_2$ (11 mg, 0.05 mmol) and Ag$_2$O (495 mg, 4.0 mmol) in DMSO (5 mL), 2 (1.54 g, 4.0 mmol) was added under N2. The reaction mixture was stirred for 10 h at 80° C., the residues were dissolved in DCM (20 mL) and washed with water (3×20 mL). The combined organic phase was washed with brine and dried over Na$_2$SO$_4$ and concentrated under reduced pressure. The residue was purified by silica gel chromatography with eluting (eluent: n-hexane) to give 3a as a yellow solid. (566 mg, 60%). $^1$H NMR (400 MHz, CDCl$_3$): δ 7.93 (s, 2H), 2.59 (d, J=7.2 Hz, 4H), 1.80-1.70 (m, 2H), 1.40-1.15 (m, 48H), 0.90-0.75 (m, 12H). $^{19}$F NMR (376 MHz, CDCl$_3$): δ−128.14 (s, 2F). $^{13}$C NMR (100 MHz, CDCl$_3$): δ 149.54 (dd, J=258.9, 20.3 Hz), 148.26, 141.70, 132.25, 130.99, 124.83, 115.13 (t, J=3.6 Hz), 110.85 (d, J=8.6 Hz), 38.53, 34.08, 33.35, 31.94, 30.05, 29.73, 29.69, 29.67, 29.39, 26.56, 22.71, 14.13. HRMS (MALDI+) Calcd for C$_{46}$H$_{68}$Br$_2$F$_2$N$_2$S$_3$ (M$^+$): 940.2879, Found: 940.2875.

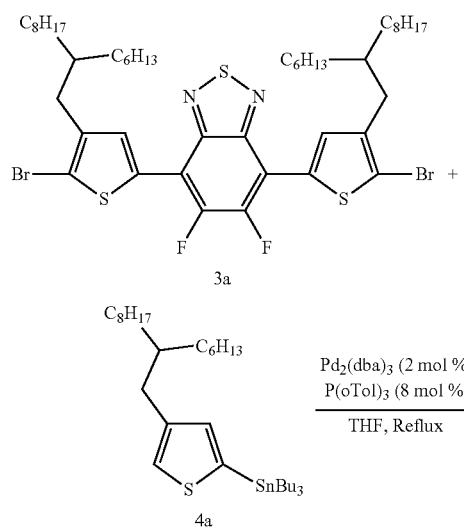

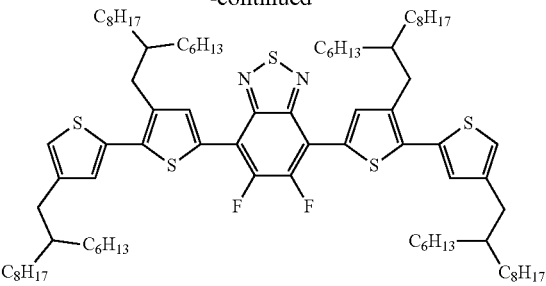

5,6-Difluoro-4,7-bis(3,4'-bis(2-hexyldecyl)-[2,2'-bithiophen]-5-yl)-2,1,3-benzothiadiazole (8)

To a solution of 3a (377 mg, 0.4 mmol), Pd$_2$(dba)$_3$ (7 mg, 0.008 mmol) and P(o-tol)$_3$ (10 mg, 0.03 mmol) in 10 mL THF was added 4a (598 mg, 1.0 mmol) under N$_2$, the reaction was refluxed overnight. After the reaction mixture was cooled to r.t. then the solvent was evaporated. The residue was purified by flash column chromatography (eluent: n-hexane) to give 8 as a red oil (475 mg, 85%). $^1$H NMR (400 MHz, CDCl$_3$): δ 8.09 (s, 2H), 7.06 (s, 2H), 6.92 (s, 2H), 2.79 (d, J=7.2 Hz, 4H), 2.68 (d, J=6.8 Hz, 4H), 1.83-1.75 (m, 2H), 1.72-1.65 (m, 2H), 1.43-1.15 (m, 96H), 0.92-0.75 (m, 24H). $^{19}$F NMR (376 MHz, CDCl$_3$): 5-128.31 (s, 2F). $^{13}$C NMR (100 MHz, CDCl$_3$): δ 149.54 (dd, J=258.9, 20.3 Hz), 148.9, 142.5, 138.8, 133.7, 135.0, 134.6, 129.0, 128.5, 121.6, 111.2, 38.9, 38.8, 35.0, 33.8, 33.5, 33.4, 32.0, 30.1, 29.8, 29.7, 29.6, 29.4, 26.7, 26.6, 26.5, 26.4, 22.7, 14.1. HRMS (MALDI+) Calcd for C$_{86}$H$_{138}$F$_2$N$_2$S$_5$ (M$^+$): 1396.9432, Found: 1397.0106.

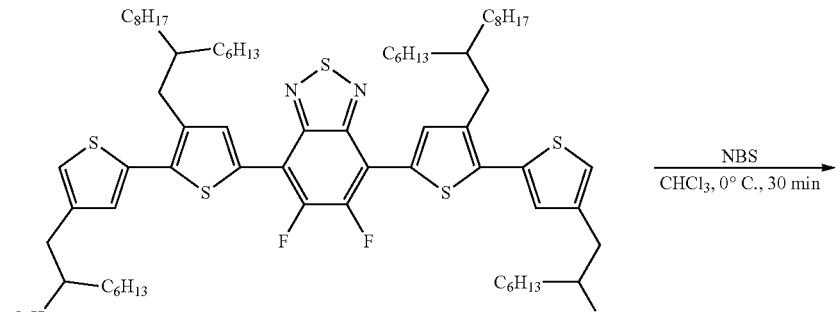

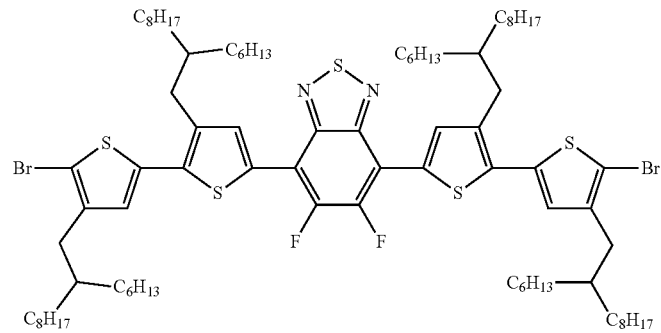

5,6-difluoro-4,7-bis(5'-bromo-3,4'-bis(2-hexyldecyl)-[2,2'-bithiophen]-5-yl)-2,1,3-benzothiadiazole (6)

To a solution of 5 (280 mg, 0.2 mmol) in 5 mL CHCl$_3$ was added NBS (71 mg, 0.4 mmol) at 0° C., the reaction was stirred for 30 min then the solvent was evaporated. The residue was purified by flash column chromatography (eluent: n-hexane) to give 6 as a red oil (250 mg, 80%). $^1$H NMR (400 MHz, CDCl$_3$) δ 8.07 (s, 2H), 6.91 (s, 2H), 2.75 (d, J=7.2 Hz, 4H), 2.52 (d, J=6.8 Hz, 4H), 1.85-1.65 (m, 4H), 1.43-1.15 (m, 96H), 0.92-0.75 (m, 24H). $^{19}$F NMR (376 MHz, CDCl$_3$): δ −128.04 (s, 2F). $^{13}$C NMR (100 MHz, CDCl$_3$) δ 149.2 (dd, J=259.0, 20.4 Hz), 148.2, 141.2, 138.7, 134.2, 133.9, 128.8, 127.4, 110.6 (d, J=9.1 Hz), 109.5, 38.2, 37.9, 33.6, 33.2, 32.8, 31.3, 29.4, 29.1, 29.0, 28.8, 28.7, 26.0, 25.9, 25.8, 25.7, 22.1, 143.5. HRMS (MALDI+) Calcd for C$_{86}$H$_{136}$Br$_2$F$_2$N$_2$S$_5$ (M$^+$): 1552.7642, Found: 1552.6932.

EXAMPLE 2

Polymer Synthesis

To a mixture of monomer 5 (30 mg, 0.019 mmol), 5,6-difluoro-4,7-bis(5-(trimethylstannyl)thiophen-2-yl)-2,1,3-benzothia diazol (46.7 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and heated for 1 h at 160° C. in a microwave. After cooling to room temperature the reaction mixture was poured into vigorously stirring methanol and the resulting polymeric precipitate was filtered. The polymer was purified by Soxhlet extraction first in DCM, chloroform and finally chlorobenzene (24 h). The chlorobenzene fraction was concentrated by rotary evaporation, suspended in methanol and filtered to afford the polymer P1 as a dark green solid.

$^1$H NMR (400 MHz, C$_2$D$_2$Cl$_4$, 120° C.). δ 8.35 (d, J=4.0 Hz, 2H), 8.21 (s, 2H), 7.40 (d, J=4.0 Hz, 2H), 7.21 (s, 2H), 2.94 (t, J=6.8 Hz, 8H), 1.95-1.85 (m, 4H), 1.56-1.30 (m, 96H), 1.00-0.86 (m, 24H). Elem. Anal. Calcd for C$_{100}$H$_{140}$F$_4$N$_4$S$_8$: C, 69.40; H, 8.15; N, 3.24, Found: C, 69.52; H, 8.41; N, 3.31. GPC Mn=72.2 kDa; Mw=129.6 kDa; PDI=1.80.

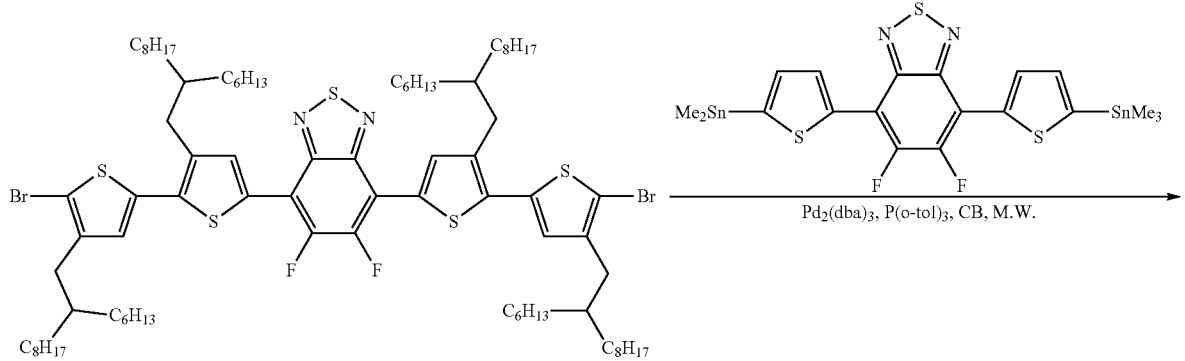

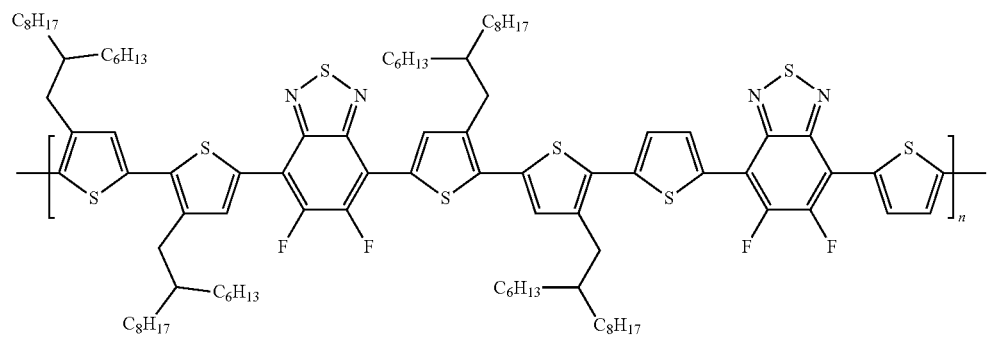

P1

EXAMPLE 3

Synthesis of Monomers

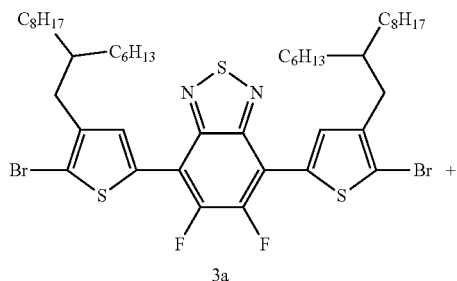

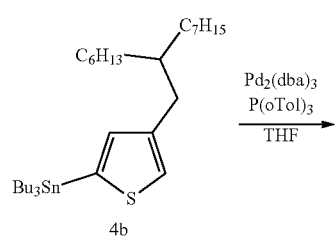

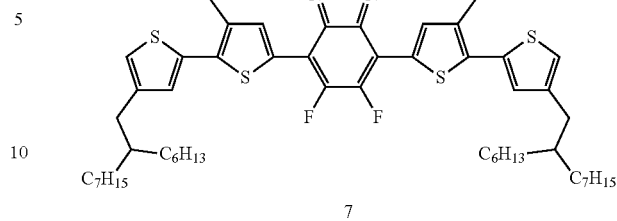

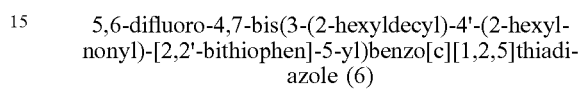

5,6-difluoro-4,7-bis(3-(2-hexyldecyl)-4'-(2-hexyl-nonyl)-[2,2'-bithiophen]-5-yl)benzo[c][1,2,5]thiadiazole (6)

To a solution of 3a (376 mg, 0.4 mmol), Pd$_2$(dba)$_3$ (7 mg, 0.008 mmol) and P(o-tol)$_3$ (10 mg, 0.03 mmol) in 10 mL THF was added 4b (540 mg, 1.0 mmol) under N$_2$, the reaction was refluxed overnight. After the reaction mixture was cooled to r.t. then the solvent was evaporated. The residue was purified by flash column chromatography (eluent: n-hexane) to give 6 as a red oil (490 mg, 90%).

$^1$H NMR (400 MHz, CDCl$_3$): δ 8.08 (s, 2H), 7.06 (s, 2H), 6.92 (s, 2H), 2.79 (d, J=7.2 Hz, 4H), 2.57 (d, J=6.8 Hz, 4H), 1.83-1.74 (m, 2H), 1.72-1.65 (m, 2H), 1.43-1.15 (m, 92H), 0.92-0.75 (m, 24H). $^{19}$F NMR (376 MHz, CDCl$_3$): δ −128.21 (s, 2F). $^{13}$C NMR (100 MHz, CDCl$_3$): 149.2 (dd, J=259.0, 20.4 Hz), 148.2, 141.2, 138.7, 134.2, 133.9, 128.8, 127.4, 110.6 (d, J=9.1 Hz), 109.5, 39.0, 38.8, 35.0, 33.8, 33.4, 32.0, 30.1, 29.8, 29.4, 26.7, 26.5, 26.4, 22.8, 22.7, 14.2; HRMS (MALDI+) Calcd for C$_{84}$H$_{134}$F$_2$N$_2$S$_5$ (Mt): 1368.9119, Found: 1368.9110.

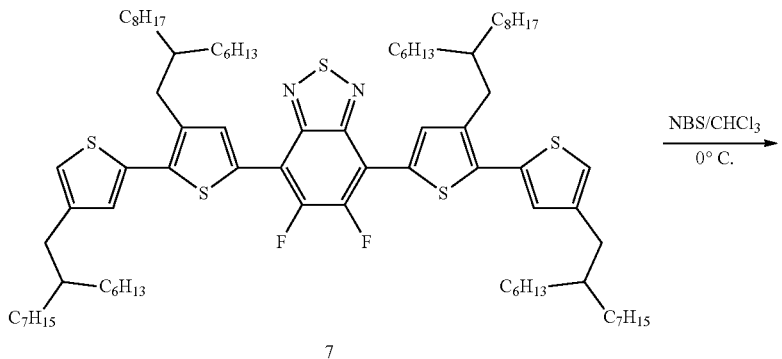

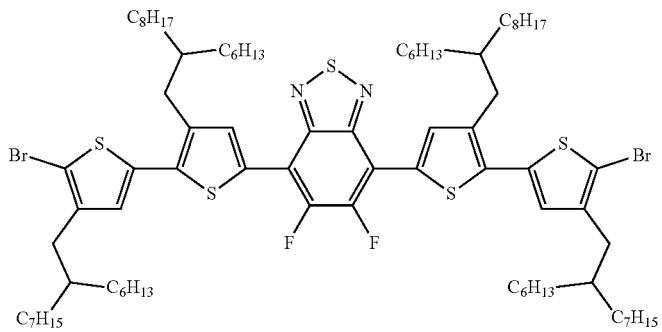

5,6-Difluoro-4,7-bis(5'-bromo-3-(2-hexyldecyl)-4'-(2-hexylnonyl)-[2,2'-bithiophen]-5-yl)-2,1,3-benzothiadiazol (8)

To a solution of 7 (275 mg, 0.2 mmol) in 5 mL CHCl$_3$ was added NBS (71 mg, 0.4 mmol) at 0° C., the reaction was stirred for 30 min then the solvent was evaporated. The residue was purified by flash column chromatography (eluent: n-hexane) to give 8 as a red oil (260 mg, 85%). $^1$H NMR (400 MHz, CDCl$_3$): δ 8.07 (s, 2H), 6.91 (s, 2H), 2.75 (d, J=7.2 Hz, 4H), 2.52 (d, J=7.2 Hz, 4H), 1.85-1.65 (m, 4H), 1.41-1.15 (m, 92H), 0.93-0.78 (m, 24H). $^{19}$F NMR (376 MHz, CDCl$_3$): δ −128.03 (s, 2F). $^{13}$C NMR (100 MHz, CDCl$_3$): δ 149.2 (dd, J=259.0, 20.5 Hz), 148.7, 141.8, 139.2, 134.9, 134.6, 129.4, 127.9, 111.0 (d, J=9.1 Hz), 110.1, 38.9, 38.6, 34.2, 33.8, 33.4, 32.0, 30.1, 29.8, 29.7, 29.4, 26.7, 26.6, 26.5, 22.7, 14.2. HRMS (MALDI+) Calcd for C$_{84}$H$_{132}$Br$_2$F$_2$N$_2$S$_5$ (M$^+$): 1524.7329, Found: 1554.7357.

EXAMPLE 4

Polymer Synthesis

To a mixture of monomer 8 (30 mg, 0.02 mmol), 5,6-difluoro-4,7-bis(5-(trimethylstannyl)thiophen-2-yl)-2,1,3-benzothiadiazol (13.3 mg, 0.02 mmol), Pd$_2$(dba)$_3$ (0.4 mg, 0.0004 mmol) and P(o-tol)$_3$ (0.6 mg, 0.002 mmol) was added 0.2 mL of chlorobenzene in a glove box protected with N$_2$. The reaction mixture was then sealed and heated for 1 h at 160° C. in a microwave reactor. After cooling to room temperature the reaction mixture was poured into vigorously stirring methanol and the resulting polymeric precipitate was filtered. The polymer was purified by Soxhlet extraction first in DCM, chloroform and finally chlorobenzene (24 h). The chlorobenzene fraction was concentrated by rotary evaporation, suspended in methanol and filtered to afford the polymer as a dark green solid (28 mg, 85%).

$^1$H NMR (400 MHz, C$_2$D$_2$Cl$_4$, 120° C.). δ 8.35 (d, J=4.0 Hz, 2H), 8.21 (s, 2H), 7.40 (d, J=4.0 Hz, 2H), 7.21 (s, 2H), 2.95 (t, J=6.8 Hz, 8H), 1.95-1.85 (m, 4H), 1.56-1.30 (m, 92H), 1.00-0.86 (m, 24H). Elem. Anal. Calcd for C$_{98}$H$_{136}$F$_4$N$_4$S$_8$: C, 69.13; H, 8.05; N, 3.29, Found: C, 68.99; H, 8.20; N, 3.26. GPC Mn=66.1 kDa; Mw=109.6 kDa; PDI=1.66.

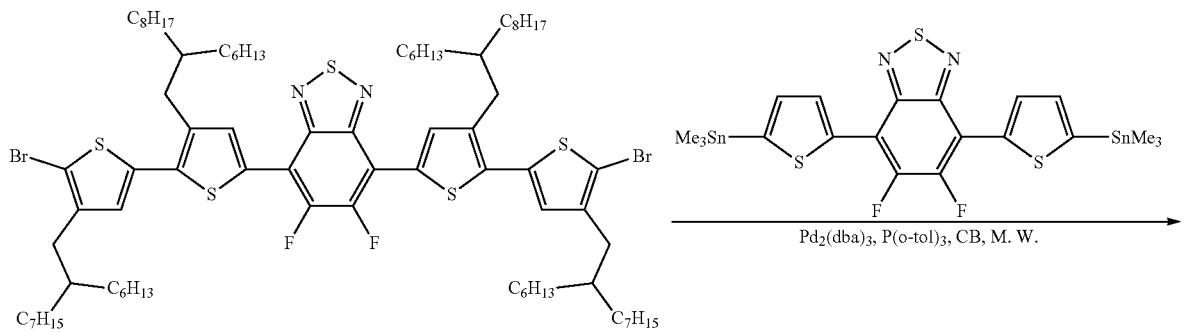

8

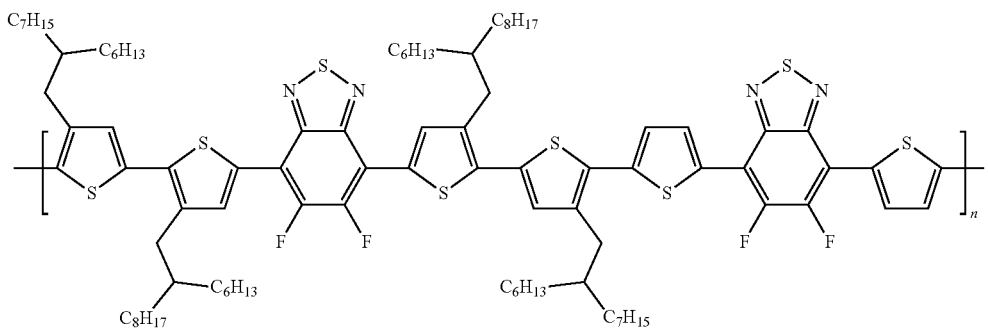

P2

COMPARATIVE EXAMPLE 1

Polymer Synthesis

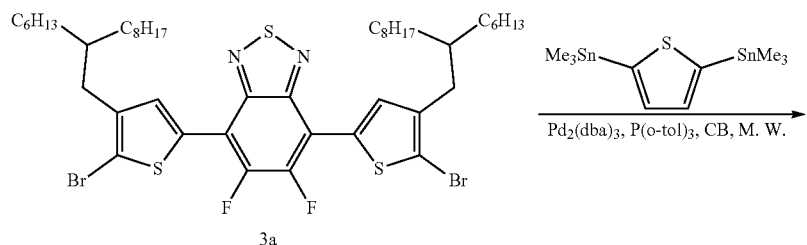

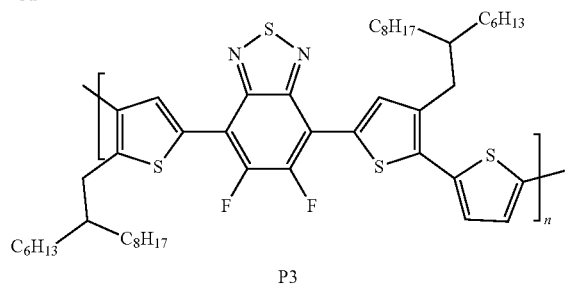

P3

To a mixture of monomer 3a (94.3 mg, 0.1 mmol), 2,5-bis(trimethylstannyl)thiophene (41.0 mg, 0.095 mmol), Pd$_2$(dba)$_3$ (1.8 mg, 0.002 mmol) and P(o-tol)$_3$ (2.4 mg, 0.008 mmol) was added 1.6 mL of chlorobenzene in a glove box protected with N$_2$. The reaction mixture was then sealed and heated for 1 h at 160° C. in a microwave reactor. After cooling to room temperature the reaction mixture was poured into vigorously stirring methanol and the resulting polymeric precipitate was filtered. The polymer was purified by Soxhlet extraction first in DCM, chloroform and finally chlorobenzene (24 h). The chlorobenzene fraction was concentrated by rotary evaporation, suspended in methanol and filtered to afford the polymer as a dark green solid (59 mg, 68%). $^1$H NMR (400 MHz, C$_2$D$_2$Cl$_4$, 120° C.). 58.22 (s, 2H), 7.34 (s, 4H), 2.96 (d, J=6.4 Hz, 4H), 1.95-1.85 (m, 2H), 1.56-1.30 (m, 48H), 1.00-0.84 (m, 12H). Elem. Anal. Calcd for C$_{50}$H$_{70}$F$_2$N$_2$S$_4$: C, 69.40; H, 8.15; N, 3.24, Found: C, 69.29; H, 8.31; N, 3.22. GPC M$_n$=37.7 kDa; M$_w$=55.9 kDa; PDI=1.48.

COMPARATIVE EXAMPLE 2

Polymer Synthesis

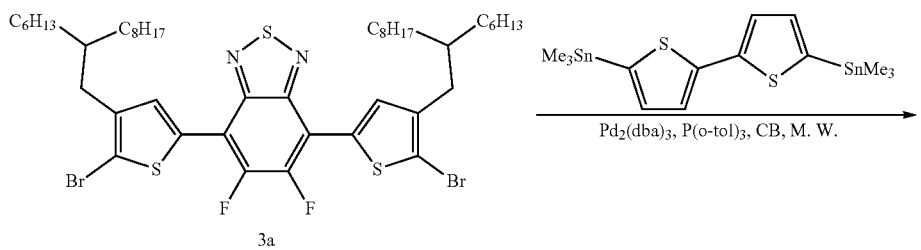

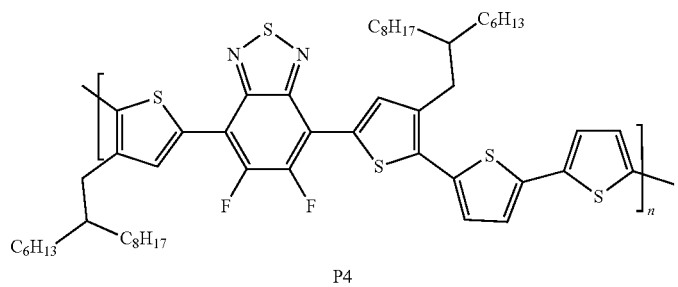

P4

To a mixture of monomer 3a (94.3 mg, 0.1 mmol), 5,5'-bis(trimethylstannyl)-2,2'-bithiophene (49.2 mg, 0.1 mmol), Pd$_2$(dba)$_3$ (1.8 mg, 0.002 mmol) and P(o-tol)$_3$ (2.4 mg, 0.008 mmol) was added 1.6 mL of chlorobenzene in a glove box protected with N$_2$. The reaction mixture was then sealed and heated for 1 h at 160° C. in a microwave reactor. After cooling to room temperature the reaction mixture was poured into vigorously stirring methanol and the resulting polymeric precipitate was filtered. The polymer was purified by Soxhlet extraction first in DCM, chloroform and finally chlorobenzene (24 h). The chlorobenzene fraction was concentrated by rotary evaporation, suspended in methanol and filtered to afford the polymer as a dark green solid (70 mg, 74%). $^1$H NMR (400 MHz, C$_2$D$_2$Cl$_4$, 120° C.). δ 8.21 (s, 2H), 7.27 (br, 4H), 2.94 (d, J=6.8 Hz, 4H), 1.95-1.85 (m, 2H), 1.56-1.30 (m, 48H), 1.00-0.86 (m, 12H). Elem. Anal. Calcd for C$_{54}$H$_{72}$F$_2$N$_2$S$_5$: C, 68.45; H, 7.66; N, 2.96. Found: C, 68.23; H, 7.79; N, 2.89. GPC Mn=65.6 kDa; M$_w$=110.9 kDa; PDI=1.69.

COMPARATIVE EXAMPLE 3

Synthesis of Monomers

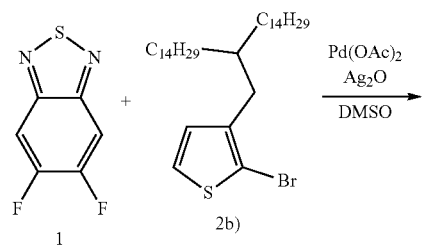

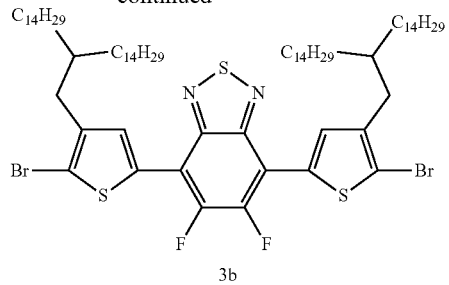

5,6-Difluoro-4,7-bis(5-bromo-4-(2-tetradecylhexadecyl)-2-thienyl)-2,1,3-benzothiadiazole (3b)

To a solution of 1 (172 mg, 1.0 mmol), Pd(OAc)$_2$ (11 mg, 0.05 mmol) and Ag$_2$O (495 mg, 4.0 mmol) in DMSO (5 mL), 2b (2.33 g, 4.0 mmol) was added under N$_2$. The reaction mixture was stirred for 10 h at 80° C., the residues were dissolved in DCM (20 mL) and washed with water (3×20 mL). The combined organic phase was washed with brine and dried over Na$_2$SO$_4$ and concentrated under reduced pressure. The residue was purified by silica gel chromatography with eluting (eluent: n-hexane) to give 3b as a yellow solid. (467 mg, 35%). $^1$H NMR (400 MHz, CDCl$_3$): δ 7.94 (s, 2H), 2.59 (d, J=7.2 Hz, 4H), 1.80-1.70 (m, 2H), 1.40-1.15 (m, 96H), 0.90-0.75 (m, 12H); $^{13}$C NMR (100 MHz, CDCl3): δ 149.58 (dd, J=258.9, 20.3 Hz), 148.26, 141.70, 132.39, 131.04, 115.13, 111.1, 38.53, 34.14, 33.37, 31.94, 30.01, 29.72, 29.68, 29.39, 26.55, 22.71, 14.13. HRMS (MALDI+) Calcd for C$_{46}$H$_{68}$Br$_2$F$_2$N$_2$S$_3$ (M+): 1332.7261, Found: 1332.7250.

COMPARATIVE EXAMPLE 4

Polymer Synthesis

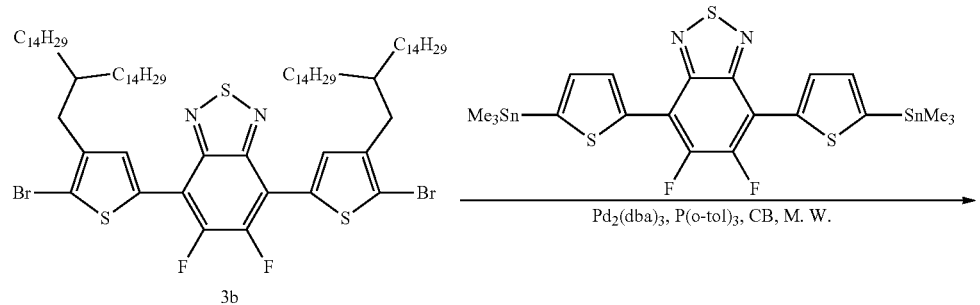

To a mixture of monomer 3b (66.6 mg, 0.05 mmol), 5,6-difluoro-4,7-bis(5-(trimethylstannyl)thiophen-2-yl)-2,1,3-benzothiadiazol (33.1 mg, 0.05 mmol), Pd$_2$(dba)$_3$ (0.9 mg, 0.001 mmol) and P(o-tol)$_3$ (1.2 mg, 0.004 mmol) was added 1.6 mL of chlorobenzene in a glove box protected with N$_2$. The reaction mixture was then sealed and heated for 1 h at 160° C. in a microwave reactor. After cooling to room temperature the reaction mixture was poured into vigorously stirring methanol and the resulting polymeric precipitate was filtered. The polymer was purified by Soxhlet extraction first in DCM, chloroform and finally chlorobenzene (24 h). The chlorobenzene fraction was concentrated by rotary evaporation, suspended in methanol and filtered to afford the polymer as a dark green solid (30 mg, 40%). Elem. Anal. Calcd for C$_{88}$H$_{128}$F$_4$N$_4$S$_6$: C, 69.98; H, 8.54; N, 3.71, Found: C, 69.69; H, 8.80; N, 3.68. GPC M$_n$=58.3 kDa; M$_w$=98.0 kDa; PDI=1.68.

EXAMPLE 5

Synthesis of Monomers

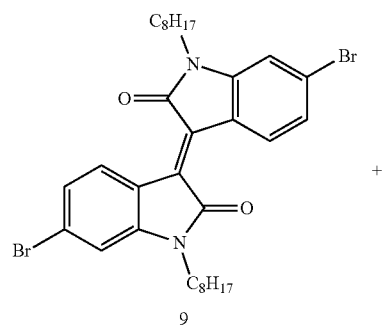

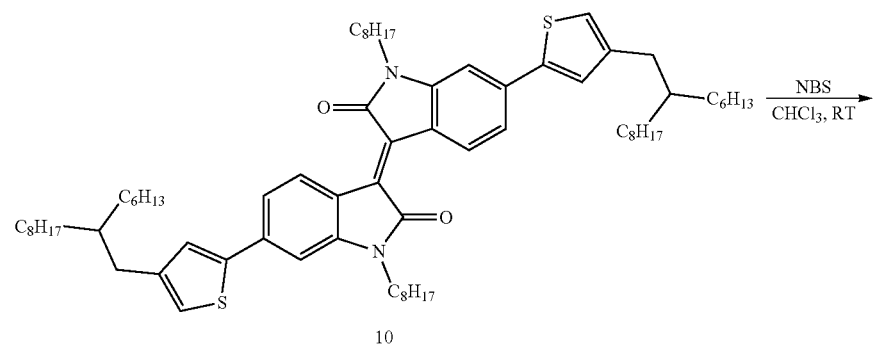

(E)-1,1'-dioctyl-6,6'-bis(4-(2-hexyldecyl)thiophen-2-yl)-[3,3'-biindolinylidene]-2,2'-dione (10)

To a solution of 9 (258 mg, 0.4 mmol), Pd$_2$(dba)$_3$ (7 mg, 0.008 mmol) and P(o-tol)$_3$ (10 mg, 0.03 mmol) in 20 mL toluene was added 4b (600 mg, 1.0 mmol) under N$_2$, the reaction was refluxed overnight. After the reaction mixture was cooled to r.t., a solution of KF in water was added and the organic phase was washed with water for three times, then dried with Na$_2$SO$_4$. The solvent was evaporated and the residue was purified by flash column chromatography (eluent: n-hexane/DCM=3:1) to give 10 as a dark solid (330 mg, 75%). $^1$H NMR (400 MHz, CDCl$_3$): δ 9.16 (d, J=8.4 Hz, 2H), 7.28 (dd, J=8.4 Hz, 1.6 Hz, 2H), 7.22 (d, J=1.6 Hz, 2H), 6.95 (s, 2H), 6.92 (s, 2H), 3.81 (t, J=7.2 Hz, 4H), 2.52 (d, J=6.8 Hz, 4H), 1.75-1.65 (m, 6H), 1.43-1.15 (m, 68H), 0.92-0.75 (m, 18H). $^{13}$C NMR (100 MHz, CDCl$_3$): δ 168.3, 145.3, 143.5, 143.4, 138.2, 131.9, 130.3, 126.2, 121.8, 121.0, 119.2, 104.6, 40.1, 38.8, 35.1, 33.3, 31.9, 30.1, 29.7, 29.6, 29.4, 29.3, 29.2, 27.6, 27.1, 26.6, 22.7, 22.6, 14.1, 14.0. HRMS (MALDI+) Calcd for C$_{72}$H$_{110}$N$_2$O$_2$S$_2$ (M$^+$): 1098.8009, Found: 1098.8006.

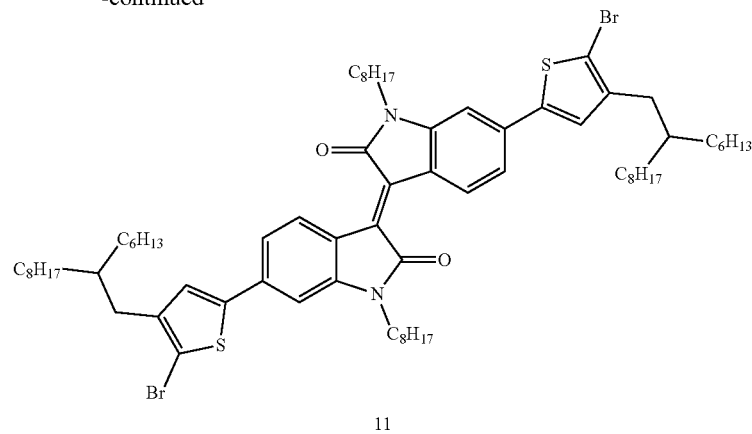

11

(E)-6,6'-bis(5-bromo-4-(2-hexyldecyl)thiophen-2-yl)-1,1'-dioctyl-[3,3'-biindolinylidene]-2,2'-dione (11)

To a solution of 10 (210 mg, 0.2 mmol) in 10 mL CHCl$_3$ was added NBS (71 mg, 0.4 mmol) at 0° C., the reaction was stirred overnight, the mixture was washed with water for three times, then dried with Na$_2$SO$_4$. The solvent was evaporated and the residue was purified by flash column chromatography (eluent: n-hexane/DCM=3:1) to give 11 as a dark red solid (200 mg, 80%). $^1$H NMR (400 MHz, CDCl$_3$) δ 9.17 (d, J=8.4 Hz, 2H), 7.19 (d, J=8.4 Hz, 2H), 7.06 (s, 2H), 6.85 (s, 2H), 3.81 (t, J=7.2 Hz, 4H), 2.52 (d, J=6.8 Hz, 4H), 1.75-1.65 (m, 6H), 1.43-1.15 (m, 66H), 0.92-0.75 (m, 18H). $^{13}$C NMR (100 MHz, CDCl$_3$) δ 168.2, 145.4, 143.0, 142.8, 137.2, 131.9, 130.5, 125.6, 121.2, 118.8, 110.6, 104.2, 40.1, 38.6, 34.4, 33.4, 31.9, 30.1, 29.7, 29.6, 29.4, 29.3, 29.2, 27.6, 27.0, 26.5, 22.7, 22.6, 14.1, 14.0; HRMS (MALDI+) Calcd for C$_{72}$H$_{198}$Br$_2$N$_2$O$_2$S$_2$ (M$^+$): 1254.6219, Found: 1254.6213.

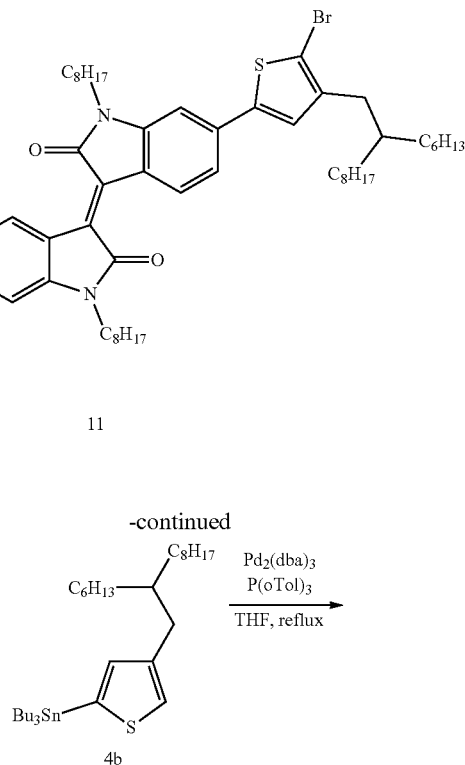

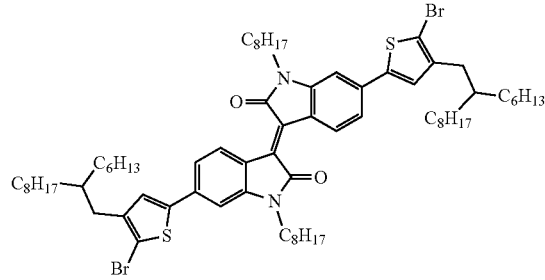

11

+

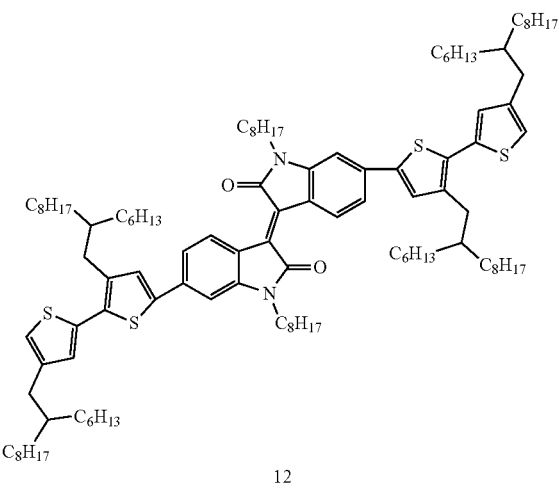

12

(E)-6,6'-bis(4,4'-bis(2-hexyldecyl)-[2,2'-bithiophen]-5-yl)-1,1'-dioctyl-[3,3'-biindolinylidene]-2,2'-dione (12)

To a solution of 11 (500 mg, 0.4 mmol), Pd$_2$(dba)$_3$ (7 mg, 0.008 mmol) and P(o-tol)$_3$ (10 mg, 0.03 mmol) in 10 mL THF was added 4b (540 mg, 1.0 mmol) under N$_2$, the reaction was refluxed overnight. After the reaction mixture was cooled to r.t. then the solvent was evaporated. The residue was purified by flash column chromatography (eluent: n-hexane) to give 12 as a dark red oil (560 mg, 82%). $^1$H NMR (400 MHz, CDCl$_3$) δ 9.18 (d, J=8.4 Hz, 2H), 7.20 (d, J=8.4 Hz, 2H), 7.09 (s, 2H), 7.06 (s, 2H), 6.93 (s, 2H), 6.86 (s, 2H), 3.83 (t, J=7.2 Hz, 4H), 2.73 (d, J=6.8 Hz, 4H), 2.52 (d, J=6.8 Hz, 4H), 1.75-1.65 (m, 8H), 1.43-1.15 (m, 120H), 0.95-0.75 (m, 30H).

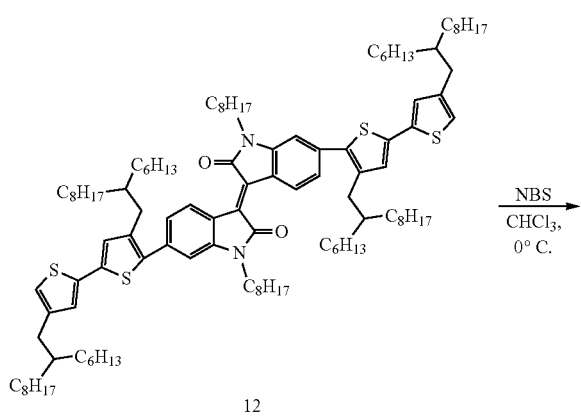

12

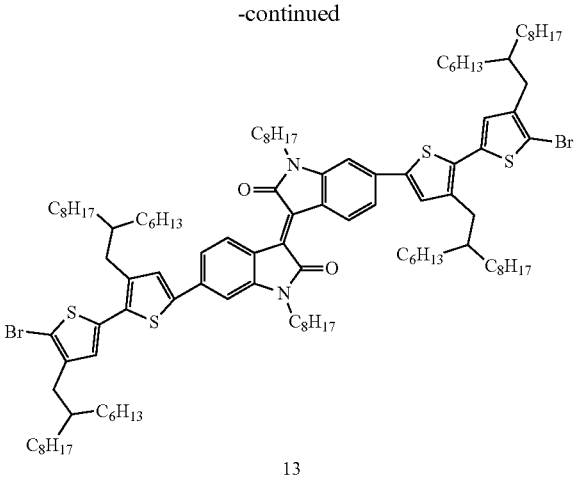

13

To a solution of 12 (342 mg, 0.2 mmol) in 10 mL CHCl$_3$ was added NBS (71 mg, 0.4 mmol) at 0° C., the reaction was stirred for 30 min then the solvent was evaporated. The residue was purified by flash column chromatography (eluent: n-hexane) to give 13 as a dark red oil (310 mg, 83%). $^1$H NMR (400 MHz, CDCl$_3$) δ 9.18 (d, J=8.4 Hz, 2H), 7.19 (d, J=8.4 Hz, 2H), 7.05 (s, 2H), 6.94 (s, 2H), 6.83 (s, 2H), 3.83 (t, J=7.2 Hz, 4H), 2.73 (d, J=6.8 Hz, 4H), 2.52 (d, J=6.8 Hz, 4H), 1.75-1.65 (m, 8H), 1.43-1.15 (m, 120H), 0.95-0.75 (m, 30H).

EXAMPLE 6

Polymer Synthesis

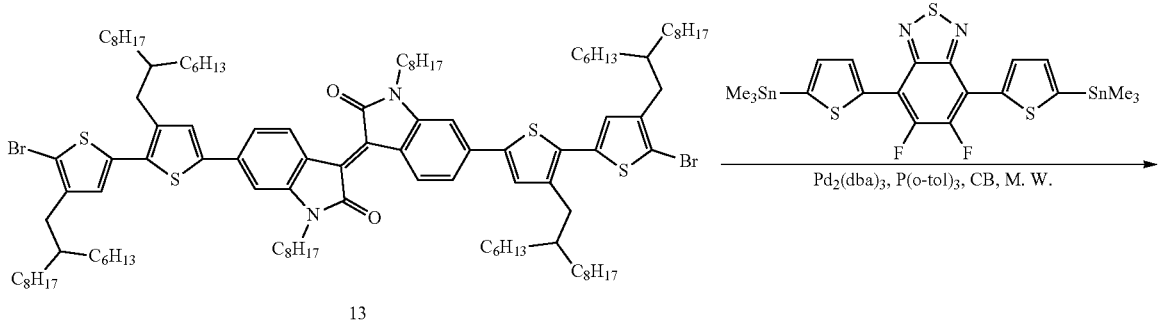

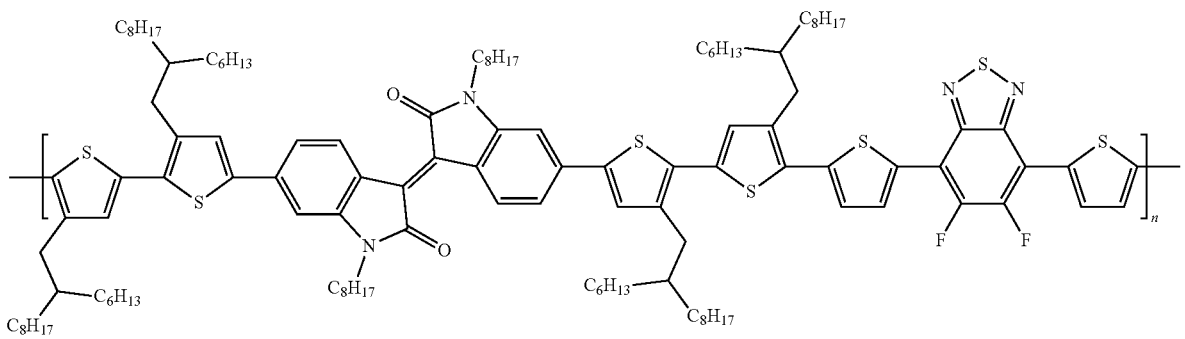

P6

To a mixture of monomer 13 (37.4 mg, 0.02 mmol), 5,6-difluoro-4,7-bis(5-(trimethylstannyl)thiophen-2-yl)-2,1,3-benzothiadiazol (13.2 mg, 0.02 mmol), Pd$_2$(dba)$_3$ (0.9 mg, 0.001 mmol) and P(o-tol)3 (1.2 mg, 0.004 mmol) was added 1.6 mL of chlorobenzene in a glove box protected with N2. The reaction mixture was then sealed and heated for 1 h at 160° C. in a microwave reactor. After cooling to room temperature the reaction mixture was poured into vigorously stirring methanol and the resulting polymeric precipitate was filtered. The polymer was purified by Soxhlet extraction first in DCM and then chloroform. The chlorobenzene fraction was concentrated by rotary evaporation, suspended in methanol and filtered to afford the polymer as a dark green solid (28 mg, 70%).

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A conjugated polymer containing 5 or more repeating units of Formula (II):

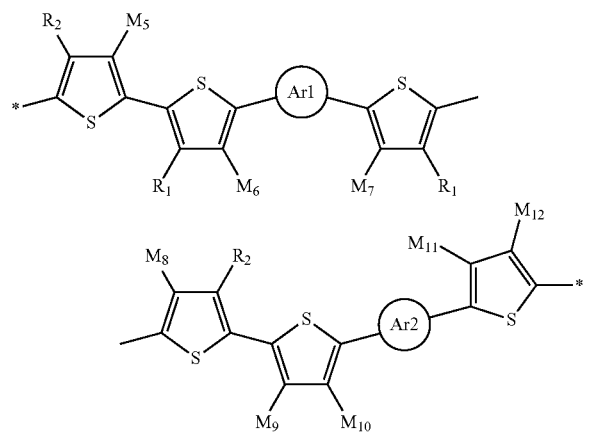

Formula (II)

wherein Ar1 and Ar2 are aromatic units that are not thiophene, wherein a * bond is a bond to an additional unit of Formula (II) and there are three thiophene units between each Ar1 unit and Ar2 unit in the conjugated polymer, Ar1 and Ar2 are different from each other and independently selected from:

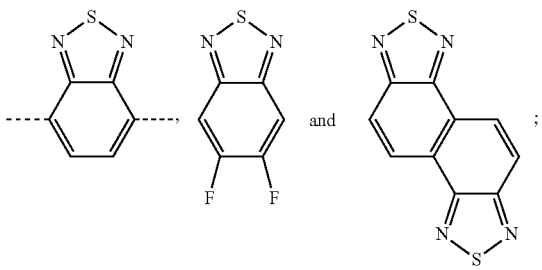

M5, M6, M7, M8, M9, M$_{10}$, M$_{11}$, M$_{12}$ are H atom; and

R$_1$ and R$_2$ are independently selected from branched alkyl groups with 6-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups.

2. A composition comprising the conjugated polymer of claim 1 dissolved or dispersed in a liquid medium without using any processing additives.

3. An optical, electronic, or optoelectronic device comprising the conjugated polymer of claim 1.

4. The device of claim 3, wherein the device is selected from an organic field-effect transistor, an organic light-emitting transistor, and an organic photovoltaic device.

* * * * *